(12) United States Patent
Galkin et al.

(10) Patent No.: US 11,998,961 B2
(45) Date of Patent: Jun. 4, 2024

(54) ENDOSCOPE CLEANING WITH VISCOELASTIC LIQUID

(71) Applicant: SABAN VENTURES PTY LIMITED, Alexandria (AU)

(72) Inventors: Alexander Galkin, Lane Cove West (AU); Stefan Gebhardt, Lane Cove West (AU); Ashwin Gopalan Nair, Lane Cove West (AU); Brian Hingley, Lane Cove West (AU); Joshua Storm Caley, Lane Cove West (AU)

(73) Assignee: Saban Ventures Pty Limited, Macquarie Park (AU)

( * ) Notice: Subject to any disclaimer, the term of this patent is extended or adjusted under 35 U.S.C. 154(b) by 407 days.

(21) Appl. No.: 17/285,897

(22) PCT Filed: Oct. 16, 2019

(86) PCT No.: PCT/AU2019/051124
§ 371 (c)(1),
(2) Date: Apr. 15, 2021

(87) PCT Pub. No.: WO2020/077403
PCT Pub. Date: Apr. 23, 2020

(65) Prior Publication Data
US 2021/0370362 A1    Dec. 2, 2021

(30) Foreign Application Priority Data
Oct. 16, 2018    (AU) .................................. 2018903910

(51) Int. Cl.
*A61L 2/18*      (2006.01)
*B08B 9/027*    (2006.01)
(Continued)

(52) U.S. Cl.
CPC .............. *B08B 9/0326* (2013.01); *A61L 2/18* (2013.01); *B08B 9/027* (2013.01); *B08B 9/032* (2013.01);
(Continued)

(58) Field of Classification Search
CPC ............. B08B 3/00–14; B08B 9/00–46; A61L 2/00–28; A61L 2202/24; A61B 90/70; A61B 2090/701; A61B 1/00–32
See application file for complete search history.

(56) References Cited

U.S. PATENT DOCUMENTS

| | | | |
|---|---|---|---|
| 2014/0370067 A1* | 12/2014 | Margraf | .................... A61L 2/18 |
| | | | 546/264 |
| 2018/0094214 A1 | 4/2018 | Labib et al. | |

(Continued)

FOREIGN PATENT DOCUMENTS

| | | |
|---|---|---|
| EP | 3357520 A1 | 8/2018 |
| WO | 2019113634 A1 | 6/2019 |

OTHER PUBLICATIONS

International Search Report, PCT/AU2019/051124, dated Dec. 24, 2019, 4 pages.
(Continued)

*Primary Examiner* — Mikhail Kornakov
*Assistant Examiner* — Richard Z. Zhang
(74) *Attorney, Agent, or Firm* — Edell, Shapiro & Finnan, LLC

(57) ABSTRACT

The invention relates to compositions and methods for reducing biocontaminant (for example flesh, blood, mucous, faeces or biofilm) on a surface, such as an endoscope surface. The compositions are viscoelastic and of low lubricity, having the following properties at 21° C.: a rotational yield point between 140% strain and 300% strain; a peak viscosity between 550 Pa·s and 2000 Pa·s; an oscillatory
(Continued)

Mechanism of viscoelastic liquid action flow point between 250 and 700% strain; and a coefficient of friction $\mu$ which has a maximum value (preferably 0.06 or greater) in the viscoelastic liquid's elastohydrodynamic region.

19 Claims, 14 Drawing Sheets

(51) Int. Cl.
    *B08B 9/032*     (2006.01)
    *C11D 3/12*     (2006.01)
    *C11D 3/22*     (2006.01)
    *C11D 3/37*     (2006.01)
    *C11D 3/386*     (2006.01)

(52) U.S. Cl.
    CPC ............ *C11D 3/1213* (2013.01); *C11D 3/124* (2013.01); *C11D 3/222* (2013.01); *C11D 3/3765* (2013.01); *C11D 3/386* (2013.01); *A61L 2202/17* (2013.01); *A61L 2202/24* (2013.01); *B08B 2209/032* (2013.01); *C11D 2111/14* (2024.01)

(56) References Cited

U.S. PATENT DOCUMENTS

2018/0249704 A1\*   9/2018   Man ...................... A01N 25/02
2018/0280587 A1   10/2018   Yano et al.

OTHER PUBLICATIONS

Written Opinion, PCT/AU2019/051124, dated Dec. 24, 2019, 9 pages.
Walker T. W. et al. "Enhanced particle removal using viscoelastic fluids" Journal of Rheology, 2014, vol. 58, pp. 63-88.
Hsu, T. T. "Surface cleaning technology using non-Newtonian fluids" Ph D Thesis (2012) Stanford University, Stanford, California, USA, 196 pages.
ANON: "Viscosity of Carbopol® Polymers in Aqueous Systems" Technical Data Sheet TDS-730, 2010, Lubrizol Advanced Materials, 10 pages.
Extended European Search Report in counterpart European Application No. 19872586.3-1017, dated Jun. 24, 2022, 8 pages.
Kaylon, D.M., et al., "Factors Affecting the Rheology and Processability of Highly Filled Suspensions," 2014, Annu Rev Chem Biomol Eng, 5:229-254, 30 pages.

\* cited by examiner

Figure 1: Mechanism of viscoelastic liquid action

Figure 2: Schematic diagram of the bench-top cleaning process of the endoscope model with the viscoelastic liquid

ENDOSCOPE CLEANING WITH VISCOELASTIC LIQUID

REFERENCE TO RELATED APPLICATIONS

This application is a U.S. national stage application of International Patent Application No. PCT/AU2019/051124, filed Oct. 16, 2019, which claims the benefit of Australian Patent Application No. 2018903910, filed Oct. 16, 2018, the entire disclosures of which are incorporated herein by reference.

TECHNICAL FIELD

This invention relates to methods for reducing biocontaminant on contaminated surfaces, more specifically contaminated surfaces which are difficult to clean by conventional cleaning methods, such as the interior cavities and lumens of devices, and in particular for cleaning the lumens, cylinders, valve sockets and connectors of contaminated medical instruments. However, it will be appreciated that the invention is not limited to this particular field of use.

BACKGROUND

An endoscope is an elongated tubular instrument that may be rigid or flexible and which incorporates an optical or video system and light source. Typically, an endoscope is configured so that one end can be inserted into the body of a patient via a surgical incision or via one of the natural openings of the body. Internal structures near the inserted end of the endoscope can be thus be viewed by an external observer.

As well as being used for investigation, endoscopes are also used to carry out diagnostic and surgical procedures. Endoscopic procedures are increasingly popular as their minimally invasive nature provides a better patient outcome (through reduced healing time and exposure to infection) enabling hospitals and clinics to achieve higher patient turnover.

Endoscopes typically take the form of a long tube-like structure with a 'distal tip' at one end for insertion into a patient and a 'connector end' at the other with a control handle located near the centre of the length. Typically, the connector end is hooked up to a supply of light, water, suction and pressurised air. The control handle is held by the operator during the procedure to control the endoscope via valves and control wheels. The distal tip contains the camera lens, lighting, nozzle exits for air and water, exit point for suction and forceps. All endoscopes have internal channels used either for delivering air and/or water, providing suction or allowing access for forceps and other medical equipment required during the procedure. Some of these channels run from one end of the endoscope to the other while others run via valve sockets at the control handle. Some channels bifurcate while others join from two into one. Endoscopes used for diagnostic or surgical purposes contain a long, narrow lumen (sometimes referred to as a forceps channel) through which surgical apparatus can pass. The apparatus can be used to remove diseased tissue or collect tissue samples for diagnosis. The collected tissue is then removed from the endoscope by drawing it outwards through the lumen. As a consequence, the lumen can become contaminated with traces of tissue from the patient. Blood, mucus and faecal matter, which are all forms of biocontaminant and can harbour bioburden, can also readily find their way into the lumen.

The high cost of endoscopes means they must be re-used. Because of the need to avoid cross infection from one patient to the next, each endoscope must be thoroughly cleaned and disinfected or sterilised after each use. This involves the cleaning of not only the outer skin of the endoscope, but also cleaning and disinfecting the lumen. Endoscopes used for colonoscopic procedures are approximately two meters long and have one or more lumen channels of diameter no more than a few millimetres. Ensuring that such long narrow channels are properly cleaned and disinfected between patients presents a considerable challenge. The challenge of cleaning is also made more difficult by the fact that there is not just one configuration for endoscopes. There are a variety of endoscopic devices suited to the particular cavity to be investigated i.e. colonoscopes inserted into the colon, bronchoscopes inserted into the airways and gastroscopes for investigation of the stomach. Gastroscopes, for instance, are smaller in diameter than colonoscopes; bronchoscopes are smaller again and shorter in length while duodenoscopes have a different tip design to access the bile duct. Some endoscopes, such as duodenoscopes, also possess a "blind lumen", closed at one end which can be even more difficult to clean.

A variety of options are available to mechanically remove biological residues from the lumen which is the first stage in the cleaning and disinfection process. By far the most common procedure for cleaning the lumens uses small brushes mounted on long, thin, flexible lines. Brushing is the mandated means of cleaning the lumen in some countries. These brushes are fed into the lumens while the endoscope is submerged in warm water and a cleaning solution. The brushes are then pushed/pulled through the length of the lumens in an effort to scrub off the soil/biocontaminant. Manual back and forth scrubbing is required. Water and cleaning solutions are then flushed down the lumens. These flush-brush processes are repeated three times or until the endoscope reprocessing technician is satisfied that the lumen is clean. At the end of this cleaning process air is pumped down the lumens to dry them. A flexible pull-through having wiping blades may also be used to physically remove material. A liquid flow through the lumen at limited pressure can also be used. In general, only the larger suction/biopsy lumens can be cleaned by brushing or pull throughs. Air/water channels are too small for brushes, so these lumens are usually only flushed with water and cleaning solution.

After mechanical cleaning, a chemical clean is carried out to remove the remaining biological contaminants. Because endoscopes are sensitive and expensive apparatus, the biological residues cannot be treated at high temperatures or with strong chemicals. For this reason, the mechanical cleaning needs to be as thorough as possible. In many cases, the current mechanical cleaning methodologies fail to fully remove biofilm from lumens, particularly where cleaning relies on liquid flow alone. Regardless of how good the conventional cleaning processes are it is almost inevitable that a small microbial load will remain in the channel of the lumen. There has been significant research to show that the method of cleaning with brushes, even when performed as prescribed, does not completely remove biofilm in endoscope lumens.

Biofilms are a particularly challenging from of biocontaminant and start to form when a free-floating microorganism attaches itself to a surface and surrounds itself with a protective polysaccharide layer. The microorganism then multiplies, or begins to form aggregates with other microorganisms, increasing the extent of the polysaccharide layer. Multiple sites of attachment can in time join up, forming significant deposits of biofilm. Once bacteria or other microorganisms are incorporated in a biofilm, they become significantly more resistant to chemical and mechanical cleaning than they would be in their free-floating state. The organisms themselves are not inherently more resistant, rather, resistance is conferred by the polysaccharide film and the fact that microorganisms can be deeply embedded in the film and isolated from any chemical interaction. Any residual biofilm remaining after an attempt at cleaning quickly returns to an equilibrium state and further growth of microorganisms within the film continues.

As well as lacking in efficacy, particularly in respect of biofilms, the current manual brushing procedures suffer from other drawbacks. The large number of different endoscope manufacturers and models results in many minor variations of the manual cleaning procedure. This has led to confusion and ultimately poor compliance in cleaning processes. The current system of brushing is also hazardous to the endoscope reprocessing staff who clean them. Brushing can disperse small particles or aerosols of biocontaminant into the air which can be accidentally ingested or inhaled. The chemicals that are currently used to clean endoscopes can adversely affect the reprocessing staff. The current system of manual brushing is also labour intensive, leading to increased cost. Thus, the current approaches to cleaning and disinfecting the lumens in medical apparatus are still inadequate and residual microorganisms are now recognised as a significant threat to patients and staff exposed to these devices.

There is evidence of bacterial transmission between patients from inadequate cleaning and disinfection of internal structures of endoscopes which in turn has led to patients acquiring mortal infections. Between 2010 and 2015 more than 41 hospitals worldwide, most in the U.S., reported bacterial infections linked to the scopes, affecting 300 to 350 patients (http://www.modernhealthcare.com/article/20160415/NEWS/160419937). It would be expected that a reduction in the biocontaminant in various medical devices would produce a concomitant overall reduction in bioburden (the amount of pathogens) and ultimately reduce infection rates and mortality. In addition, if an endoscope is not properly cleaned and dried, biofilm can form on the interior surfaces of the device. Endoscope lumens are particularly prone to biofilm formation. They are exposed to significant amounts of biocontamination, and subsequent cleaning of the long narrow lumens is quite difficult due to inaccessibility and the inability to monitor the cleaning process. There is considerable pressure in medical facilities to reprocess endoscopes as quickly as possible. Because endoscopes are cleaned by hand, the training and attitude of the technician are important in determining the cleanliness of the device. Residual biofilm on instruments can result in a patient acquiring an endoscope acquired infection. Typically, these infections occur as outbreaks and can have fatal consequences for patients.

Biofilm can be problematic in other areas, such as in the food, beverage and air-conditioning fields. Although not subject to high loads of biocontaminants in the manner of endoscopes, fluid lines are often provided with high volumes of nutrients under ideal conditions for the formation and growth of biofilms.

Biocontamination as used herein refers to any king of material of biological origin such as biofilms and related polysaccharide matrices, blood, mucous, faeces, and proteinaceous matter, including hardened denatured proteinaceous matter and the like, or other material which is capable of harbouring bioburden or microbial material such as bacteria, viruses, fungi, spores, prions and other pathogens.

One embodiment of the present invention allows to overcome or ameliorate at least one of the disadvantages of the prior art, or to provide a useful alternative.

SUMMARY OF THE INVENTION

According to a first aspect the invention provides a method of reducing biocontaminant on a surface contaminated therewith comprising contacting the surface with viscoelastic liquid having a low lubricity, and flowing said viscoelastic liquid along said surface thereby to remove contaminant from the surface. The viscoelastic liquid is such that the flow is plug flow, rather than liquid flow.

Preferably, the viscoelastic liquid is flowed under conditions of controlled shear rate and/or strain.

According to a second aspect, the invention provides a viscoelastic liquid having a low lubricity.

In the above aspects of the invention, the viscoelastic liquid preferably has the following rheological and tribological properties at 21° C.:
 a rotational yield point between 140% strain and 300% strain;
 a peak viscosity between 550 Pa·s and 2000 Pa·s;
 an oscillatory flow point between 250 and 700% strain; and
 a coefficient of friction $\mu$ which has a maximum value in the viscoelastic liquid's elastohydrodynamic region.

The rotational yield point may be for example between 170% strain and 270% strain or between 200% strain and 250% strain.

The peak viscosity may be for example between 600 Pa·s and 1200 Pa·s.

The oscillatory flow point may be for example between 250 and 700% strain.

The coefficient of friction $\mu$ may for example have a maximum value in the range 0.005-1.0 m/s.or 0.01-0.3 m/s or 0.5 to 0.15 m/s.

The maximum value for the coefficient of friction $\mu$ is independently 0.06 or greater (for instance 0.06-1) or 0.1 or greater (for instance 0.1-1) or 0.12 or greater (for instance 0.12 or greater)

In certain embodiments, the surface cleaned by the present method may be a contaminated surface of a medical instrument.

The surface of a medical instrument may be an interior surface of a medical instrument, such as an endoscope. The interior surface may be, for example, an elongate lumen, suction valve cylinder, air/water cylinder or biopsy port.

In other embodiments, the surface may be for example the inner surface of a dental line or a line used in the preparation or dispensation of food or beverage.

The biocontaminant may be one or more of flesh, blood, mucous, faeces, biofilm or lubricant.

The viscoelastic liquid may be flowed continuously in a single direction, or the flow of the viscoelastic liquid may be pulsed. The viscoelastic liquid may be flowed alternately in different directions.

Preferably, the viscoelastic liquid has a flow rate which is at or below the maximum allowable pressure rating of the medical instrument.

Preferably, the viscoelastic liquid has a flow rate such that the elastic modulus (also sometimes referred to as the storage modulus) G' of the viscoelastic liquid exceeds the viscous modulus (also sometimes referred to as the loss modulus) G" of the viscoelastic liquid. That is, for any given viscoelastic fluid, G'>G". It is also preferred that the viscoelastic liquid is passed along the surface (or through the lumen) at a flow rate such that the shear rate of the viscoelastic liquid is below the flow point of the viscoelastic liquid.

In the case of cleaning a lumen or line, the flow rate is predetermined based upon the lumen diameter being cleaned. In general, the relationship is that for an endoscope lumen of x mm diameter, the flow rate should be in the range of 0.5 x ml/min-2 x ml/min.

Thus, for instance, for a 0.9 mm diameter lumen, the flow rate is between 0.45 ml/min and 1.8 ml/min, for a 1.45 mm diameter lumen the flow rate is between 0.8 ml/min and 2.9 ml//min and for a 4 mm lumen the flow rate is between 2 ml/min and 8 ml/min The methods of the present invention may further include one or more pre-rinsing or post-rinsing steps with water and/or enzymatic detergent.

Preferably, the viscoelastic liquid comprises one or more cationic, amphoteric, anionic or non-ionic polymers dispersed in a solvent, which for preference is water. The viscoelastic liquid may contain a dispersed high-surface area inorganic and/or organic material, for instance, a high-surface area material having a surface area of 50-600 m$^2$/g.

The viscoelastic liquid may contain dispersed abrasive particles of inorganic and/or organic materials.

However, it is important that the viscoelastic liquid of the present invention excludes microfibrils or other additives that may affect the rheology and result in the viscoelastic liquid having a liquid flow rather than a cohesive plug flow as in the case of the present invention.

In one embodiment, the contaminant is biofilm and the viscoelastic liquid contains silica particles, which may be silica nanoparticles. These are for preference hydrophilic fumed silica nanoparticles. The silica nanoparticles preferably have a particle size of 10-100 nm, more preferably 20-70 nm. The primary nanoparticles of fumed Silica may in some cases be agglomerated in micron-sized clusters. In some embodiments, the Silica content is in the range of 0.5 to 20% by weight.

The viscoelastic liquid may contain dispersing agents and or one or more surfactants and/or emulsifiers. It may contain one or more inorganic and/or organic rheology modifiers.

For preference the polymer used in the viscoelastic liquid is carbomer, crosspolymer, acrylic polymer, Guar Gum or mixture thereof. Preferably, the polymer is Polyacrylate crosspolymer-6 or carbomer, or a mixture of both.

The polymer may be synthetic or natural. The solid content of the viscoelastic liquid is between 0.1 and 40% by weight, for example, between 0.5 and 35% by weight or between 1 and 20% by weight or between 1 and 10% by weight or between 2 and 7% by weight or between 3 and 6% by weight. The polymer content is preferably in the range of 0.1 to 20% by weight, for example, between 0.1 and 5% by weight or between 0.2 and 4% by weight or between 0.5 and 3% by weight. If water is the solvent for the viscoelastic liquid, it is preferably present in an amount of 0.1-99.9%, for example between 90 and 98% by weight or between 95 and 97% by weight.

The term "viscoelastic liquid" as used herein is a mixture of one or more polymers in a solvent or carrier fluid, which in some embodiments is water, although any other suitable solvent or carrier fluid may be used.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "cleaning" as used herein is intended to refer to the removal of inorganic and organic matter, including but not limited to bio burden, microorganisms, biofilm and lubricants.

DESCRIPTION OF THE INVENTION

Figure 1:
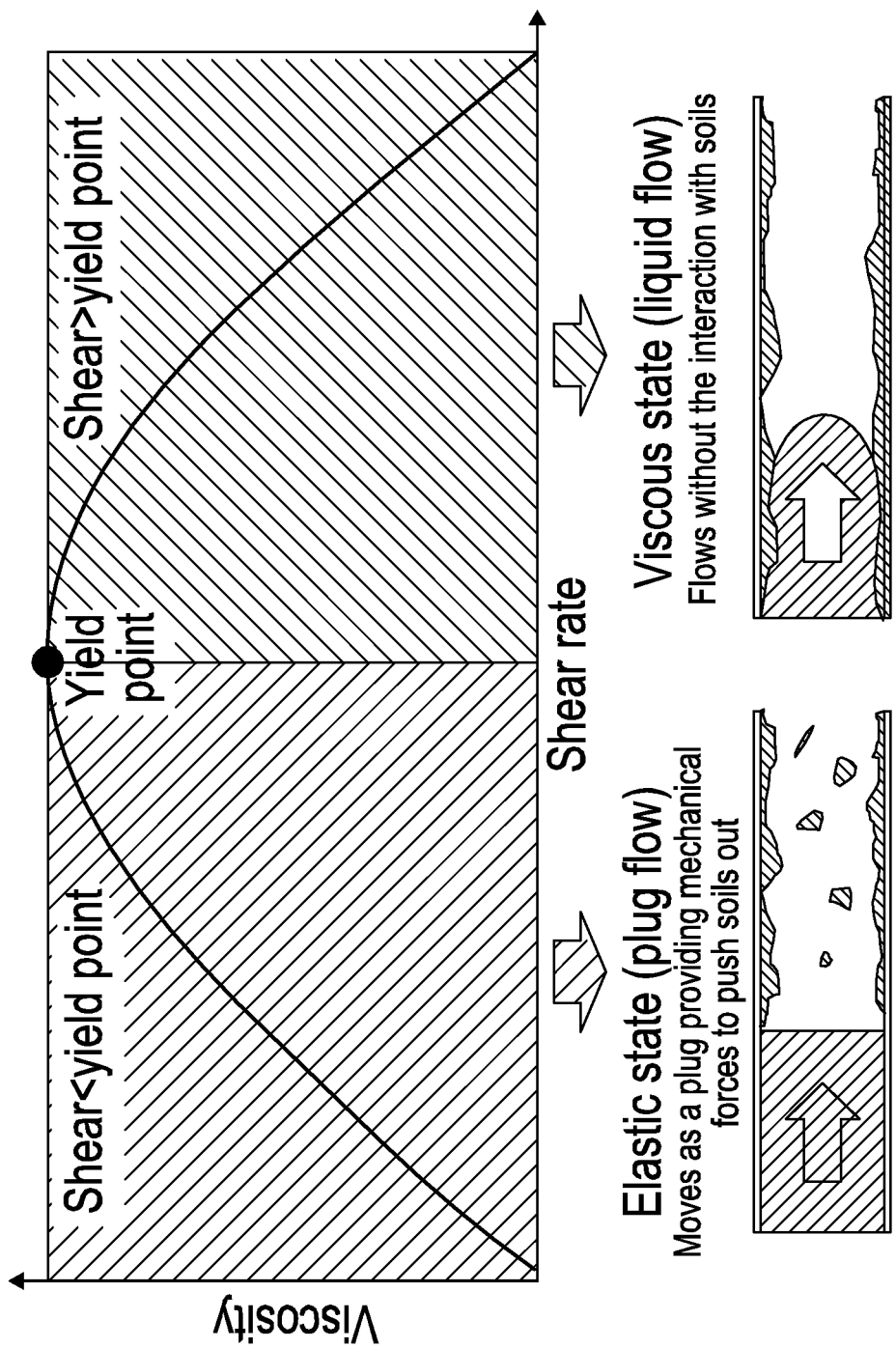
FIG. 1 shows a mechanism of viscoelastic liquid action.

Embodiments of the present disclosure relate to passing a viscoelastic liquid along a contaminated surface to remove contaminant from the surface. For instance, the viscoelastic liquid may be passed through the lumen, cylinder, valve socket or connector of an endoscope for the purposes of cleaning the endoscope channel of biocontaminant, which includes residual tissue such as flesh, blood, mucous and faeces remaining after diagnostic or surgical procedures.

In an embodiment the viscoelastic liquid comprises dissolved and/or dispersed chemicals in a carrier fluid. The carrier fluid is selected to provide a suitably stable formulation. Suitable carrier fluids include water, alcohols, glycols or their mixtures, or any other suitable fluids.

This viscoelastic liquid can be a viscoelastic polymeric water-based system or any other viscoelastic system. It may also contain additional functional additives, like rheology modifiers, high surface area inorganic materials, dispersing agents, surfactants, emulsifiers, solvents or other functional ingredients to enhance the cleaning efficacy. These can include abrasive particles or particles with adsorbent properties.

The formulations of the present invention have been shown to demonstrate cleaning efficiency which results from their rheological and tribological properties. The chemistry of each formulation has been found to be not relevant to the cleaning efficacy. As can be seen in the examples and comparative examples given below, a number of formulations were tested and it was not predictable from the composition of the formulations alone which formulations would be effective cleaning agents. For example, polyacrylate was found to be effective with fumed silica and fumed alumina, but ineffective with activated carbon. Guar gum was effective with γ-alumina, or on its own, but not when added to Carbopol, which was a component of many other effective cleaning formulations. Thus, looking solely at the chemistries of the cleaning mixtures, it is impossible to establish a coherent model for predicting cleaning.

The rheology of each sample provides some level of predictive capacity; however, it was found that there were a number of samples that possessed the rheological profile of effective cleaning formulations but which nevertheless were not particularly effective. The present inventors have established a specific hitherto unknown rheology/tribology profile that consistently provides good cleaning of lumens, as established by biological testing.

In some embodiments, the viscoelastic liquid contains other functional ingredients like rheology modifiers, high surface area adsorbing materials, surfactants, dispersing agents, emulsifiers, solvents or suspended inorganic/organic particles. This viscoelastic liquid behaves largely as fluid with the elastic modulus (G') dominating.

In one embodiment, the viscoelastic liquid is a water-based system with optimised rheology containing dispersed polymers and high surface area hydrophilic fumed silica. Nanoparticles of silica have been shown in some cases to be useful in the removal of biofilm. The process is a complex physico-chemical one and involves more than simple mechanical action. Nevertheless, other suspended solid particles, for instance crystalline silica (greater than nanoscale), calcium carbonate, activated carbon or other abrasive materials and their mixtures may be used to enhance the mechanical action of the viscoelastic liquid. Other functional additives like surfactants, solvents, emulsifiers or dispersing agents can be used as well.

The present invention also relates to the use of viscoelastic liquid to remove biofilm.

The invention will be described with reference to the use of a flowable, conveyable viscoelastic liquid for endoscope cleaning. Based on the teaching of the present invention it will be understood by those skilled in the art that the invention may be embodied in other forms and may utilise other liquids, suspensions or emulsions in the cleaning of endoscopes and other instruments without departing from the concepts herein described. For instance, the methods of the present invention are useful in cleaning other lines or surfaces susceptible to contamination. Particularly, the methods of the present invention are useful in cleaning waterlines, such as those used in the food, cosmetic, dental and beverage industries. Such lines are very susceptible to biofilm contamination.

The invention using viscoelastic liquid is described with reference to specific examples, however, it will be appreciated by those skilled in the art that the process is, in very large part, a physical process rather than a chemical process, so the exact chemical nature of the components is not critical but, rather, the resultant physical properties of the mixture that arise from the interrelationship of the components. Nevertheless, if reasonably practicable, physical action of the viscoelastic liquid can be enhanced with some chemical processes. E.g. the enzymatic detergent can be used in combination with the viscoelastic liquid to achieve some specific claims like the removal of fixed protein.

The physical properties of the mixture that give rise to the desirable cleaning effect include the rotational yield point, the peak viscosity, the oscillatory flow point and the friction factor.

The cleaning formulations of the present invention preferably have the following rheological and tribological properties at 21° C.:

a rotational yield point between 140% strain and 300% strain;

a peak viscosity between 550 Pa·s and 2000 Pa·s;

an oscillatory flow point between 250 and 700% strain; and coefficient of friction μ which has a maximum value in the viscoelastic liquid's elastohydrodynamic region.

The coefficient of friction is preferably in the range of 0.06 to 0.15 at a velocity of 0.1 m/s Being pumped at shear rates below the flow point, the viscoelastic liquid moves in its predominantly elastic state providing mechanical forces to the internal surfaces of the endoscope and pushing soils out. The viscoelastic liquid by itself has no abrasion properties. As mentioned above, other functional ingredients, e.g. hydrophilic fumed silica can be used to further optimise rheology and/or enhance cleaning efficacy via the adsorption of soils due to their high surface area, provide additional scrubbing due to their abrasive nature (such as provided by suspended crystalline inorganic materials) or work as solubilising/emulsifying ingredients (like surfactants or solvents) for the residues of lubricants in the endoscope. To achieve the desired cleaning efficacy, the flow rate of viscoelastic liquid along the surface is controlled such that the viscoelastic liquid's elastic modulus G' exceeds the viscous modulus G". If excessive shear or stress is applied to a viscoelastic liquid, it turns from an elastic state to a viscous state (G">G') and in doing so flows more like a Newtonian fluid. In such a case, there is a loss of structure and a loss of cleaning efficiency.

The peak viscosity between 550 Pa·s and 2000 Pa·s is optimised for lumens having ID's between 0.9 and 3.7 mm. Viscosities outside this range, i.e. those with higher viscosities can still provide good cleaning, however, there may be issues regarding pumpability. A cleaning agent with a peak viscosity above 2000 Pa·s will be suitable for 3.7 mm lumens or larger, but may have limited pumpability through a 0.9 mm lumen if remaining within the pressure range specified by the endoscope manufacturer. In the case of a viscoelastic liquid, any combination of chemicals that serves to provide the desired viscoelastic rheology profile (G'/G" ratio, yield point, viscosity, thixotropy, recovery time after the shear stress) may be used.

The tribology of the formulations of the present invention is also important. Particularly, it is important that each formulation of the present invention showed a maximum in their coefficient of friction when the mixture was in a condition of elastohydrodynamic friction. This particular region is well understood by those familiar with tribology and the information is typically presented in a Stribeck curve, as discussed in more detail below.

In combination with other functional ingredients, the preferable solid content is in the range of 0.1 to 40% by weight. The viscoelastic liquid can be water based or other media can be used to disperse/dissolve the polymers and functional ingredients. The viscoelastic liquid may include just one polymer or a combination of several polymers or contain in addition any inorganic/organic rheology modifiers to change one or more properties such as G' (elastic modulus), G" (viscous modulus), yield point, viscosity, thixotropic properties, lubricating properties, recovery time after the shear stress, temperature sensitivity of the rheology properties, shear thinning or shear thickening behaviour. The polymer may have anionic, cationic, nonionic or amphoteric nature and be, for example, any carbomer or cross-linked acrylic polymer. Other inorganic and/or organic materials, for example hydrophilic fumed Silica, can also be used as rheology modifiers to achieve the desired viscoelastic profile.

In another embodiment of the present invention the viscoelastic liquid cleaning can be combined with a chemical and/or enzymatic clean to complement the physical cleaning of the viscoelastic liquid. The chemical and/or enzymatic cleaning may be conducted before and/or after pumping the viscoelastic liquid or may involve intermediate rinsing. Additional rinsing with water and/or drying steps may be carried out as necessary.

The nature of additives, including the surface area, morphology, crystallinity, particle size, particle size distribution, emulsification properties and suspending properties have also been shown to contribute to the cleaning effect. The additives may be for example hydrophilic fumed silica grades (nanocrystalline or larger sized) or suspended insoluble particles (like crystalline silica, crystalline alumina, crystalline zirconia, activated carbon, calcium carbonate, or ceramics), sodium acrylate, anionic, amphoteric and non-ionic surfactants or their mixtures. Again, the density, nature, size, morphology and concentration of additives can be selected for optimal cleaning. For example, wetting behaviour of viscoelastic fluids can be tuned with ethoxylated fatty alcohols. On the other hand, an additional efficacy in the removal of oils and lubricants can be granted with non-ionic or anionic emulsifiers. And the use of suspended inorganic crystalline abrasive particles can enhance the cleaning efficacy in removal of fixed protein. Importantly, the abrasion properties will depend strongly on particle sizes and hardness of suspended particles.

The invention will be described with reference to the conveyable viscoelastic liquid being conveyed by pumping (i.e. pushed) but a conveyable viscoelastic liquid may equally be conveyed by way of reduced pressure or suction (i.e. pulled).

When viscoelastic liquid is used, the solid fraction is between 0.1 and 40% w/w, more particularly between 0.2 and 15% w/w and even more particularly between 0.4 and 5% w/w. The viscoelastic liquid needs to flow through all lumens of the endoscope independently on their internal diameter and it is desirable to have a viscosity and yield value that allows good flowability and pumpability in combination with a suitable viscoelastic profile, absorption, emulsification and abrasive properties. 550 to 2000 Pa·s peak viscosity at ambient temperature (as measured with Anton Paar MCR 102 modular compact rheometer) is a suitable viscosity. The desired rotational yield point at 21° C. is in the range of 140 to 300% of strain. If necessary different rheology modifiers such as fumed Silica, clays, polymers, gums, dispersing agents, electrolytes or solvents can be used to change the rheological profile of the viscoelastic liquid, such as, by modifying its viscoelastic profile, flowability, pumpability or to assist in the formation of a stable system.

It is also important that the viscoelastic liquid have the correct tribology, or friction, in combination with the correct rheology. A high friction viscoelastic liquid is desirable, for example, the viscoelastic liquid has a coefficient of friction of 0.06 or greater in the elastohydrodynamic region (the elastohydrodynamic region for any given fluid is clearly identifiable from its Stribeck curve. Typically, the elastohydrodynamic region for the viscoelastic fluids of the present invention is considered as a sliding velocity in the range between 0.004 m/s to 1.0 m/s. An overly high friction viscoelastic liquid will require higher pumping pressures, and so while useful for cleaning, may only be pumpable at pressures that exceed the manufacturer's pressure ceilings in endoscopes. The coefficient of friction $\mu$ may for example have a maximum value in the range 0.005-1.0 m/s or 0.01-0.3 m/s or 0.5 to 0.15 m/s. The maximum value for the coefficient of friction $\mu$ is independently 0.06 or greater (for instance 0.06-1) or 0.1 or greater (for instance 0.1-1) or 0.12 or greater (for instance 0.12 or greater).

For instance, the coefficient of friction $\mu$ may for example have a maximum value 0.06 or greater (for instance 0.06-1) in the range 0.005-1.0 m/s. Alternatively, the coefficient of friction $\mu$ may for example have a maximum value 0.1 or greater (for instance 0.06-1) in the range 0.01-0.3 m/s or alternatively the coefficient of friction $\mu$ may for example have a maximum value 0.12 or greater (for instance 0.06-1) in the range 0.5 to 0.15 m/s.

Typically, the coefficient of friction would usually be in the range of 0.06 to 0.15 at a velocity of 0.1 m/s.

It is necessary that the viscoelastic liquid flow across the surface in order for the surface to be cleaned. However, beyond that, it is advantageous that the viscoelastic liquid be flowed across the surface as slowly as practicable. The present inventors have established that the lower the flower rate, the better the cleaning efficacy that can be achieved. Increasing the flow rate is undesirable as it decreases the contact time available for cleaning and also because increasing the flow rate contributes overshearing of the formulation which means that at a certain point it will stop working.

It has been established that 3 ml/min is an optimal flow rate for 3.7 mm lumens in order to achieve a suitable compromise between the cleaning efficacy/cleaning agent volume and cleaning cycle time. Under standard conditions, to clean a 10 cm length of 3.7 mm lumen it is necessary to pump 30 ml of the viscoelastic liquid at 3 ml/min to get the desired cleaning efficacy. If more viscoelastic liquid is pumped, or if the flow rate is reduced the cleaning efficacy will improve but the cleaning cycle time will increase significantly. On the other hand, increased flow rate can be compensated to a certain extent by increased viscoelastic liquid volume. Also, it needs to be kept in mind that in the case of endoscopes, a manufacturer pressure ceiling exists. In practical terms, for smaller lumens (0.9 mm) the pressure ceiling is reached even at very slow flow rates of 1-2 ml/min. In general, the relationship is that for an endoscope lumen of x mm diameter, the flow rate should be in the range of 0.5 x ml/min-2 x ml/min.

It would be expected that those skilled in the art would readily be able to optimise the flow rate for any given lumen size taking into account the factors mentioned above.

Those skilled in the art will also be aware that pumping viscoelastic liquids and so on at high velocities will lead to overshearing. In the field of endoscopy, overshearing is unlikely since adherence to the pressure ceilings (as described above) would mitigate against high speed, high pressure pumping of the paste. Assuming the agent is not flowed at an oversheared velocity, the total material flow across the surface is not the main parameter driving cleaning efficiency. It is important that the cleaning agent is pumped under plug flow conditions (in the range between the yield point and flow point). FIG. 1 illustrates the difference between the plug flow of the present invention (where the fluid acts as plug or plunger to mechanically clean the lumen), and liquid flow, where the fluid simply flows around the soil with little or no interaction. For example, pumping 30 ml of paste at 3 ml/min will provide a certain cleaning efficacy, but a similar cleaning efficacy can be achieved by pumping less cleaning agent at e.g. 2 ml/min or pump more cleaning agent at e.g. 4 ml/min, for example, thus, the mass flow in all three cases will be different but cleaning efficacy can be the same.

In one embodiment, the viscoelastic liquid is premixed and provided as stable and ready to use material in a cartridge, flexible bag, bottle, canister or any other suitable packaging. The packaging containing the viscoelastic liquid is placed in line with the endoscope and the viscoelastic liquid is simply pumped from the packaging with the controlled flow rate with suitable pumps, e.g. peristaltic pumps, into lumens, cylinders, valve sockets and connectors of the endoscope as shown on FIG. 2. The viscoelastic liquid is passed through the endoscope for a suitable time to remove the biological material, depending upon the initial level of contamination and the construction of the endoscope.

Figure 2:
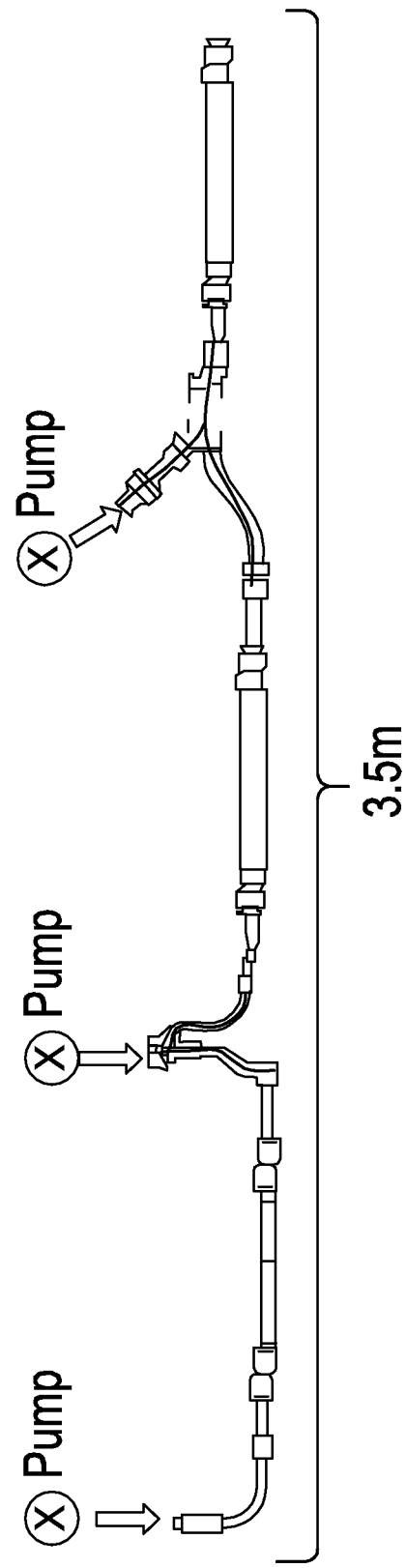
FIG. 2 shows a schematic diagram of the bench-top cleaning process of the endoscope model with the viscoelastic liquid.

The embodiment in FIG. 2 shows the bench-top model of the endoscope when the viscoelastic liquid is pumped simultaneously or sequentially through all valve sockets and connectors of the suction biopsy line. The same setup is used for the bench-top testing of air/water and auxiliary lines of the endoscope. While pumping the viscoelastic liquid the pressure sensors are used to ensure that the specified pressure ceiling is not exceeded during the endoscope cleaning process. These pressure sensors can be connected to a feedback or control mechanism to shut off the pumps should the pressure begin to approach levels that may damage the endoscope. The viscoelastic liquid flows down the desired endoscope channel and may be discharged via an exit line into a drain.

The same pumps and pressure sensors are used to provide a wash with water and/or enzymatic detergent before and/or after the physical cleaning with the viscoelastic liquid. The pre-flush and/or post-flush with water and/or enzymatic detergent is optional but it may enhance further the cleaning efficacy achieved with the viscoelastic liquid by itself, especially in the presence of hard soils like fixed proteins and/or any dry soils. The temperature of water and/or enzymatic detergent can be independently optimised by the inclusion of a thermostatic mixer, in-line heater or any other type of heater. The enzymatic detergent passes through the channels of the endoscope and may be discharged via an exit line into a drain. Once the cleaning cycle has finished, the endoscope can be purged with air or dried in any other suitable manner.

The viscoelastic liquid may also contain functional chemicals to tune its characteristics. For example, broad spectrum preservative, e.g. Phenoxy Ethanol, can be used to achieve the desired shelf life and prevent microbiological contamination of the viscoelastic liquid during handling, storage and transportation. Different absorbing materials, e.g. high surface area fumed Silica or activated Carbon can be used to enhance the cleaning efficacy via physical absorption of the soil. Surfactants, solvents or emulsifiers can be used to modify wetting behaviour and surface tension to support the removal of lubricants from the endoscope. Also suspended abrasive materials, can be used to enhance the efficacy of viscoelastic liquid in removal of hard soils like fixed proteins. For example, dispersed microcrystalline Silica (20-200 µm) supports the removal of fixed protein due to its additional abrasion properties.

EXPERIMENTAL

A number of viscoelastic fluids were prepared in accordance with the present invention, as well as some comparative examples, which had the following chemical compositions:

Example 1

| | |
|---|---|
| Carbomer (Carbopol 941) | 0.2 wt. % |
| Polyacrylate Crosspolymer-6 (Sepimax Zen) | 0.2 wt. % |
| Fumed Silica (Aerosil 380) | 3 wt. % |
| Preservative (Sepicide HB) | 0.5 wt. % |
| Water | 96.1% |
| pH | 7.5-8.5 |

Example 2

| | |
|---|---|
| Polyacrylate Crosspolymer-6 (Sepimax Zen) | 0.4 wt. % |
| Fumed Silica (Aerosil 380) | 3 wt. % |
| Preservative (Sepicide HB) | 0.5 wt. % |
| Water | 96.1 wt. % |
| pH | 7.5-8.5 |

Example 3

| | |
|---|---|
| Polyacrylate Crosspolymer-6 (Sepimax Zen) | 0.4 wt. % |
| Fumed Silica (Aerosil R816) | 3 wt. % |
| Preservative (Sepicide HB) | 0.5 wt. % |
| Water | 96.1 wt. % |
| pH | 9.1 |

Example 4

| | |
|---|---|
| Glyceryl Polyacrylate (Hispagel 200) | 6 wt. % |
| Fumed Silica (Aerosil 380) | 3 wt. % |
| Preservative (Sepicide HB) | 0.5 wt. % |
| Water | 90.5 wt. % |
| pH | 7.6 |

Example 5

| | |
|---|---|
| Carbomer (Carbopol 934) | 0.2 wt. % |
| Fumed Silica (Aerosil 380) | 2.7 wt. % |
| Preservative (Sepicide HB) | 0.5 wt. % |
| Water | 96.6 wt. % |
| pH | 7.9 |

Example 6

| | |
|---|---|
| Carbomer (Carbopol 940) | 0.12 wt. % |
| Fumed Silica (Aerosil 90) | 3 wt. % |
| Preservative (Sepicide HB) | 0.5 wt. % |

-continued

| | |
|---|---|
| Water | 96.38 wt. % |
| pH | 7.6 |

Example 7

| | |
|---|---|
| Polyacrylate Crosspolymer-6 (Septimax Zen) | 0.4 wt. % |
| Fumed Al$_2$O$_3$ (Aeroxide Alu 130) | 3 wt. % |
| Preservative (Sepicide HB) | 0.5 wt. % |
| Water | 96.1 wt. % |
| pH | 8.8 |

Example 8

| | |
|---|---|
| Guar gum | 2.5 wt. % |
| γ-Al$_2$O$_3$ (Aeroxide Alu 130) | 2 wt. % |
| Preservative (Sepicide HB) | 0.5 wt. % |
| Water | 95 wt. % |
| pH | 7.5. |

Example 9

| | |
|---|---|
| Guar gum | 2.5 wt. % |
| Preservative (Sepicide HB) | 0.5 wt. % |
| Water | 97 wt. % |
| pH | 6.0 |

Comparative Example 10

| | |
|---|---|
| Xanthan Gum | 1.6 wt. % |
| NaCl | 1.6 wt. % |
| Water | 96.8 wt. % |
| pH | ~7 |

Comparative Example 11

| | |
|---|---|
| Carbomer (Carbopol 971PNF) | 0.5 wt. % |
| Guar gum | 1 wt. % |
| Water | 98.5 wt. % |
| pH | ~7 |

Comparative Example 12

| | |
|---|---|
| Xanthan gum | 1.6 wt. % |
| Water | 98.4 wt. % |
| pH | ~7 |

Comparative Example 13

| | |
|---|---|
| Guar gum | 2 wt. % |
| Preservative (Sepicide HB) | 0.5 |
| Water | 97.5 wt. % |
| pH | 6-7 |

Comparative Example 14

| | |
|---|---|
| Polyurethane-62 (and) Trideceth-6 (Avalure TM Flex-6 Polymer) | 2 wt. % |
| Water | 98 wt. % |
| pH | 5.6 |

Comparative Example 15

| | |
|---|---|
| Carbomer (Carbopol 971P NF) | 1 wt. % |
| Water | 99 wt. % |
| pH | ~7 |

The viscoelastic fluids were prepared by the following general procedures.

In the case where a high surface area material was included (examples 1-8), the following steps were followed:

The Fumed Silica or Alumina was homogenised. The desired amount of Silica or Alumina was added to the water slowly and carefully with stirring so as to avoid the creation of dust. A dust mask and/or fume hood are recommended.

When the Silica or Alumina was sufficiently dispersed, the mixture was homogenised using a Silverson LM5-A homogenizer to properly mix the inorganic material and water. The mixture was stirred at 9000 RPM for 5 minutes, using a high shear head.

When the Silica or alumina was dispersed the polymer and preservative are added. Using the same apparatus, a general dispersion head and outer axial flow head were used. The desired amount of preservative added. The mixer was then restarted at 5000 RPM and the desired amount of polymer was added.

The pH was then measured and adjusted until it was stable within the desired limits by the addition of NaOH solution The homogeniser was then run for a further 5 minutes.

The resultant viscoelastic fluid was then stored in a glass jar with lid.

In the case of Example 9 and comparative examples 10 to 15, the process omitted the dispersion step but otherwise, the process was the same, with addition of the preservative to water and the addition polymer under stirring, followed by pH adjustment if required further stirring to ensure homogenisation.

The formulations could be prepared by simple addition of the components, with the ultimate consideration being to ensure that the components were thoroughly mixed. In those cases where solid particulate materials, such as silica was added, it was desirable to add these at the beginning of the process, as once a higher rheology mixture is formed, proper dispersal of the silica becomes more challenging. Those skilled in the art will be readily able to prepare suitably homogenised fluids.

The use of the preservative was not thought to affect the rheological or cleaning properties in any way. When using the compositions to determine the amount of cleaning and microbial reduction carried out, it is important to ensure that the test viscous fluids themselves do not introduce contamination. The viscous formulas of the present invention are believed to work as well without the addition of preservatives, however, in a practical sense, these would almost always be used to prevent the potential unwanted addition of pathogens into the system by the cleaning fluid itself.

After the fluids were prepared, the rheology and tribology of the viscoelastic fluid was characterised with MCR-102 (or MCR-302) Anton-Paar Rheometer 24 hours after the preparation.

Rheological and Tribological Properties the lines of G' and G" crossover (i.e., where the viscoelastic liquid's elastic modulus G' equals the viscous modulus G"), determines the flow point. The shear strain at the crossover point, which represents the flow point of the cleaning agent.

Figure 4:
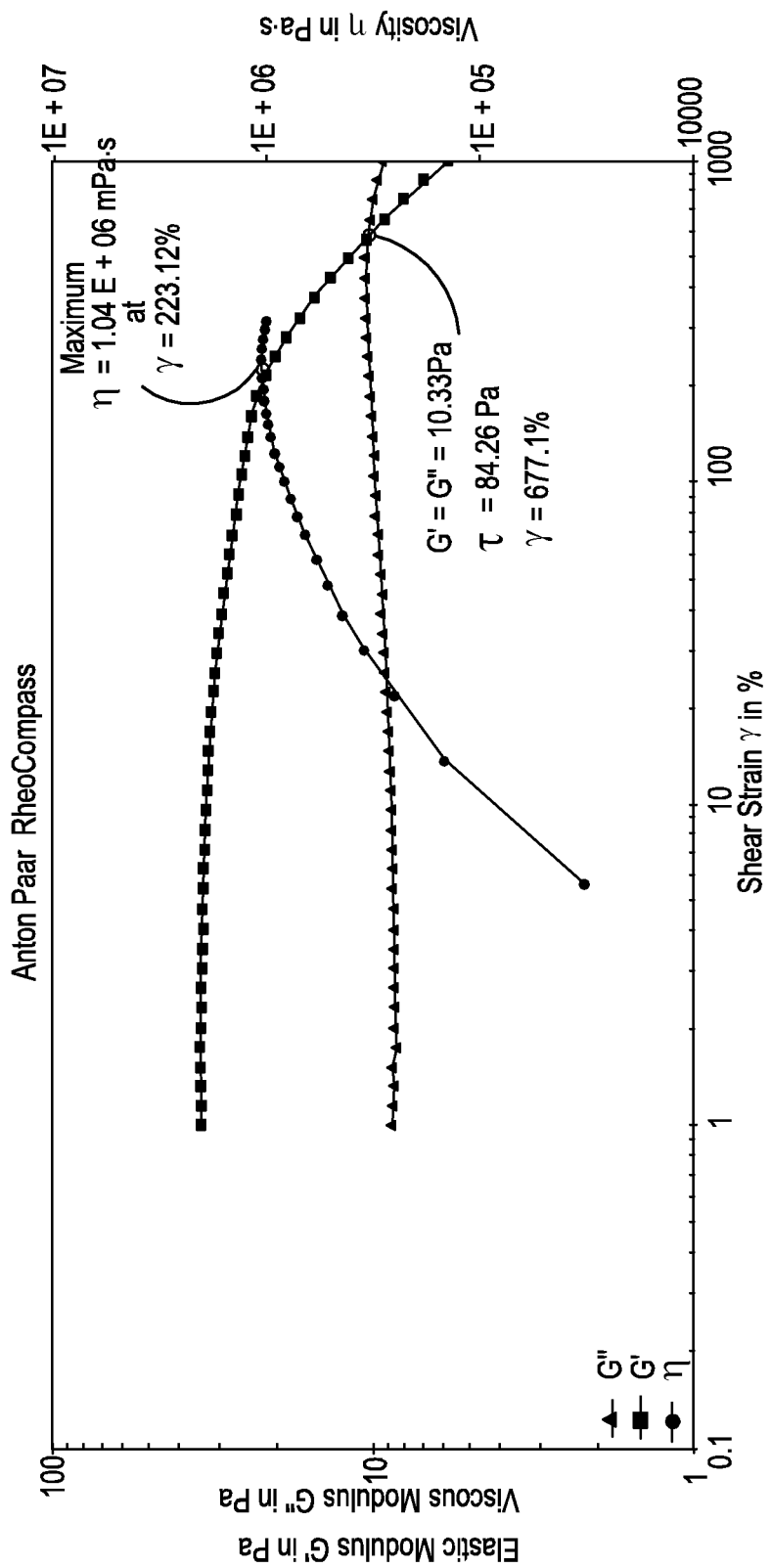
FIG. 4 shows a typical graph of a formulations of the present invention illustrating the relationship between elastic modulus G', viscous modulus G" and viscosity η.

FIG. 4 shows a typical graph of formulations of the present invention and the relation between elastic modulus, viscous modulus and viscosity. The elastic modulus G' is represented by a line with square data points. Viscous modulus G" is represented by a line with triangular data points and the viscosity is represented by circular data points. Point Z' shows the maximum eta value. Point Z" shows the crossover of G' and G", i.e. the flow point, i.e extending a line downwards from the crossover point shows a shear strain of 577% when G'=G"=10.33 Pa

| Formula | Viscosity (Pa·s) | Rotational Yield Point (% strain) | Oscillatory Flow Point (% strain) | Friction factor μ at 0.1 m/s sliding velocity | Protein Remaining (μg/cm$^2$) | Biofilm Reduction |
|---|---|---|---|---|---|---|
| Example 1 | 800-2000 | 200-300 | 500-700 | >0.06 | N/A | 7 log |
| Example 2 | 800-2000 | 200-300 | 500-700 | >0.06 | 1.1 | 5 log |
| Example 3 | 1921 | 191 | 561 | >0.06 | 5.3 | Qualitative Reduction |
| Example 4 | 1121 | 207 | 461 | >0.06 | 6.4 | Qualitative Reduction |
| Example 5 | 1366 | 191 | 467 | >0.06 | 6.3 | Qualitative Reduction |
| Example 6 | 940 | 192 | 467 | >0.06 | 0 | Qualitative Reduction |
| Example 7 | 1607 | 177 | 258 | >0.06 | 0 | Qualitative Reduction |
| Example 8 | 1708 | 314 | 561 | >0.06 | 0 | Qualitative Reduction |
| Example 9 | 1247 | 314 | 583 | >0.06 | 0.1 | Qualitative Reduction |
| Comparative Example 10 | 1570 | 240 | 666 | <0.06 | Fail | Fail |
| Comparative Example 11 | 1894 | 240 | 582 | <0.06 | Fail | Fail |
| Comparative Example 12 | 869 | 207 | 412 | 0.042 | Fail | Fail |
| Comparative Example 13 | 481 | 257 | 609 | <0.06 | Fail | Fail |
| Comparative Example 14 | 13 | n/a | n/a | n/a | Fail | Fail |
| Comparative Example 15 | 1162 | 111 | 225 | <0.06 | Fail | Fail |

Rheology Measurements

Viscosity Measurement

Viscosity was determined using a MCR102 Rheometer by Anton-Paar at 21° C. using standard operating procedures and the peak viscosity was recorded for each sample.

The stability of the formulations over time was evaluated in terms of their viscosity, rotational yield and oscillatory flow. None of the formulations exhibited a marked change in parameters over time frames of the order of weeks to months The oscillatory flow point of the sample and rotational yield point (of the sample were measured as follows:

A sample of the cleaning agent was placed in a MCR102 Rheometer by Anton-Paar. A standard test was run which determined the peak viscosity point for the sample. The shear strain at that peak viscosity was recorded. This shear strain at peak viscosity represents the yield point of the cleaning agent (Rotational yield point in the table above).

Figure 3:
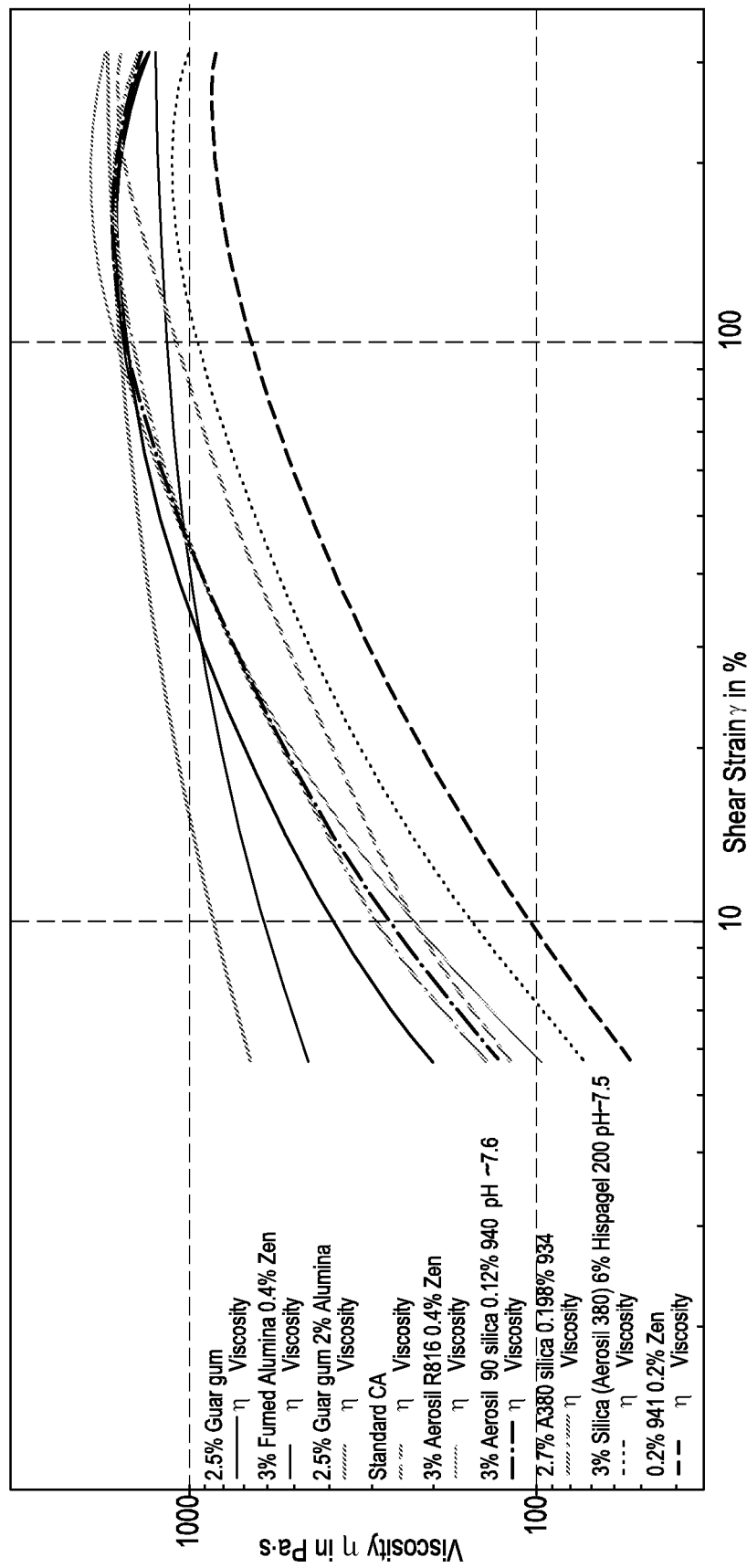
FIG. 3 shows the viscosity in Pa·s against shear strain in % for cleaning compositions of the present invention.

FIG. 3 shows the viscosity in Pa·s against shear strain in %

Figure 5:
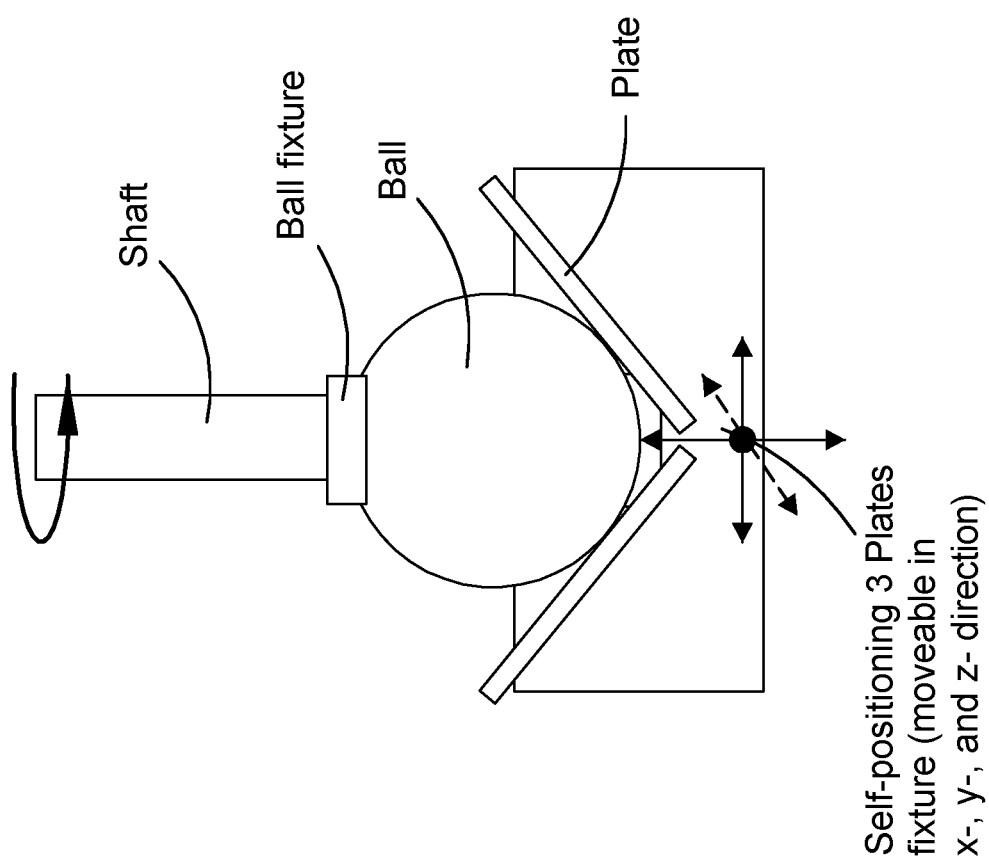
FIG. 5 shows a device for measuring tribological properties of the cleaning compositions of the present invention.

To measure the oscillating flow point of the cleaning agent, G' and G" for each sample were determined. Where Tribology The tribology of the formulations was measured using a Ball-on-3-plates device that was developed jointly by Dr Tillwich GmbH Werner Stehr and Anton Paar. The devices used were Anton-Paar MCR 102 and Anton-Paar MCR 302 rheometers. Unless otherwise stated, the measurements were taken at 21° C. and under standard laboratory conditions, i.e a typical humidity range of 30-50%. The device is shown in FIG. 5.

A sphere sits upon three self-positioning plates which are moveable in the x-, y- and z-directions. The sphere touches each plate at a single point. The sphere is attached to a shaft and can rotate in position along the axis of the shaft. Each plate continuously contacts the sphere at the same point of the plate, even though the sphere has a linear movement with respect to each plate.

The sphere contacts the plate, with normal force $F_N$. The shaft then rotates the sphere. The amount of torque required to rotate the sphere establishes the baseline friction between the plates and the sphere.

Figure 6:
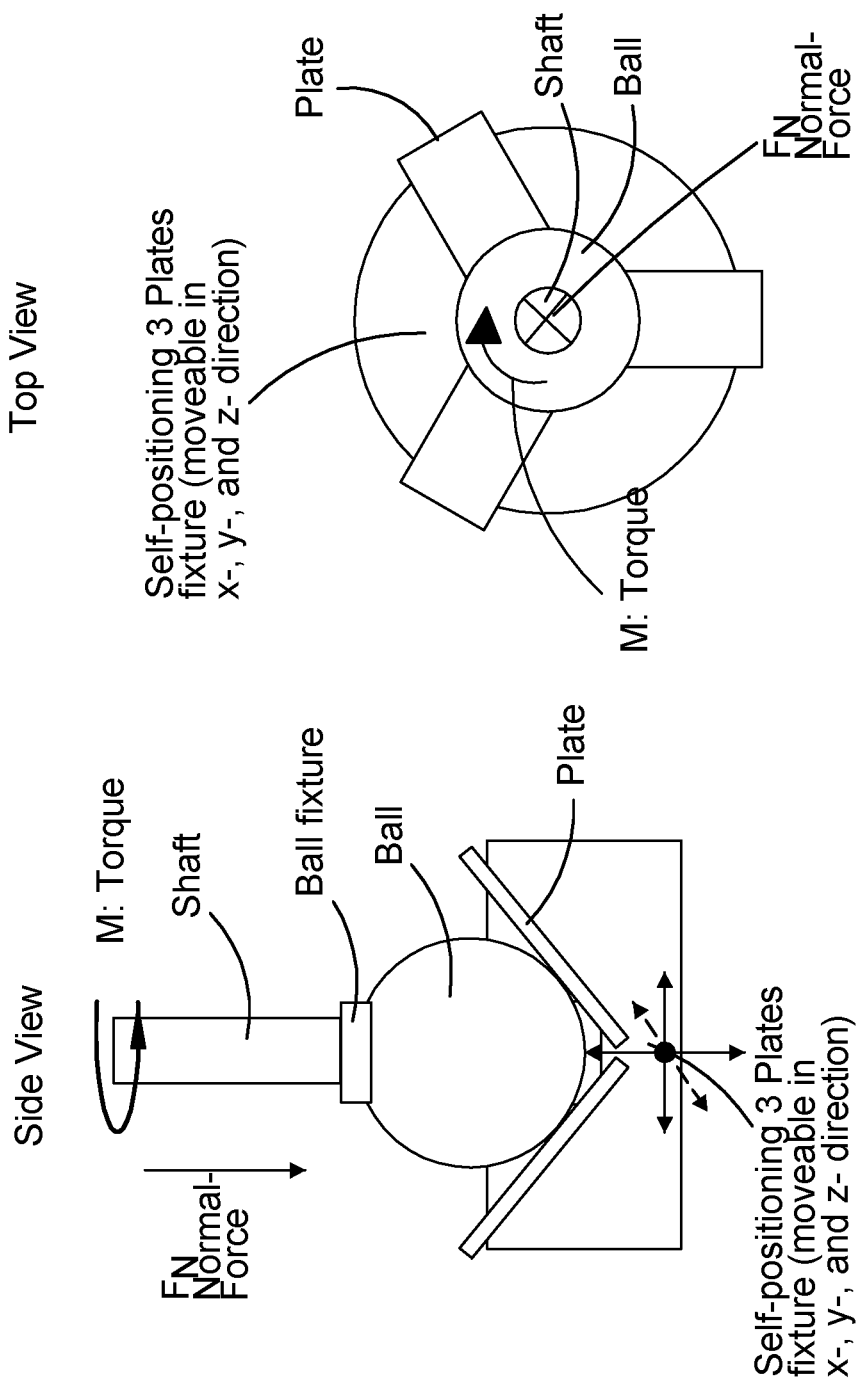
FIG. 6 shows the operation of the device for measuring tribological properties.

The sample is then placed on the plates, and in contact with the sphere, surrounding the point of contact between the sphere and each plate. The sphere is maintained towards the plates with constant normal force $F_N$. The shaft then rotates the sphere and the amount of torque required at each rotational velocity is measured. The torque required can then be used to determine the friction or lubricity provided by the sample. FIG. 6 shows the device in use.

Figure 7:
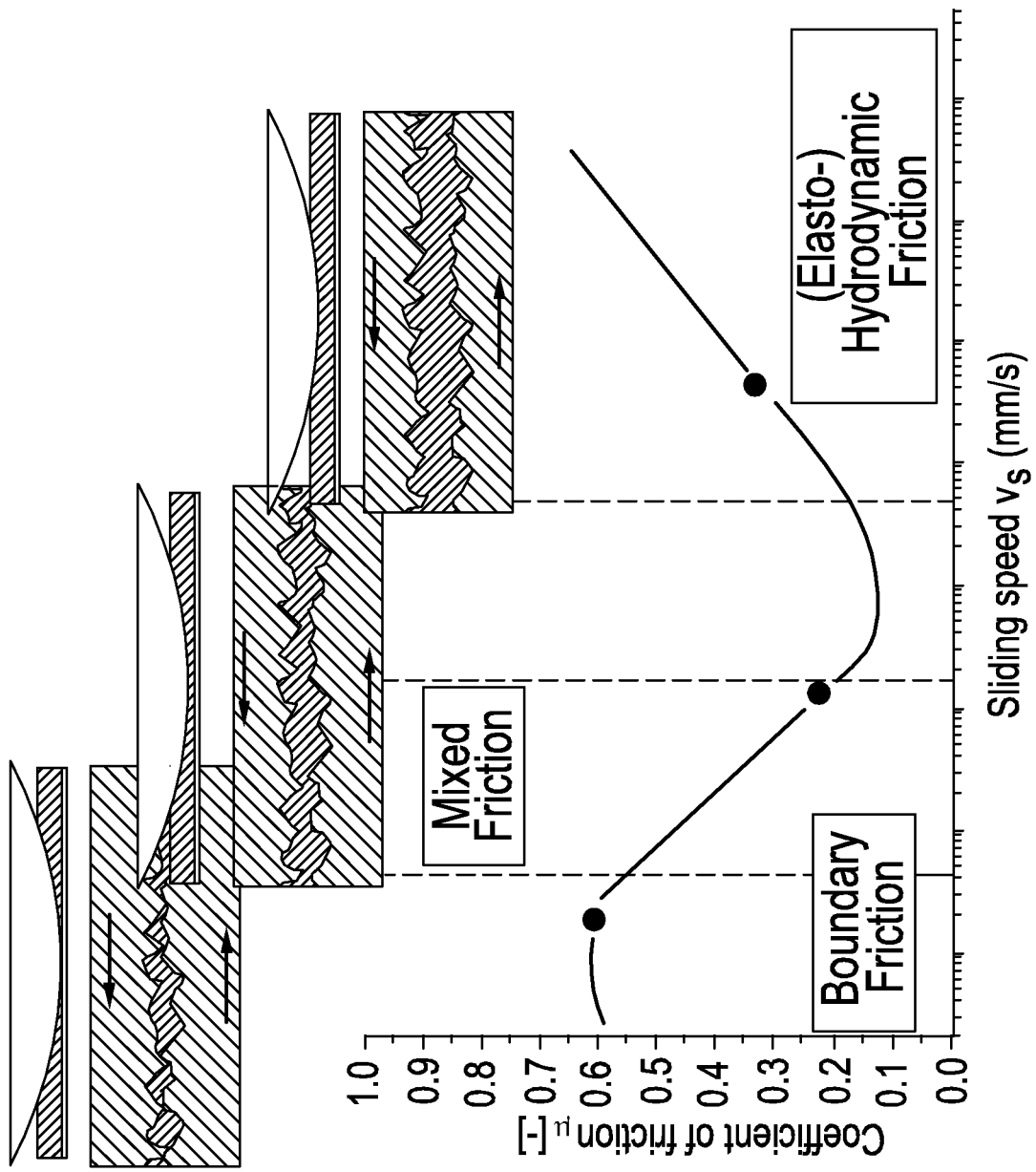
FIG. 7 shows the Stribeck curve, relating hydrodynamic viscosity with linear velocity.

It is important to measure the true hydrodynamic (or in this case, elastohydrodynamic) friction of the sample. It is well known in tribology, as illustrated by the Stribeck curve (FIG. 7), that in such systems, at low velocities, boundary friction between the two measuring surfaces will prevail as a result of the interacting surface roughness. As the velocity increases, a situation of mixed friction exists in which components of both boundary and hydrodynamic friction contribute. The coefficient of friction decreases in this speed range. The coefficient of friction begins to increase at higher velocities (higher sliding speeds) when true hydrodynamic friction takes over as the sole frictional mechanism. At higher speeds, the structure of the sample may begin to break down. The region of true hydrodynamic friction, before sample breakdown, is of interest as it establishes the inherent lubricity or otherwise of the sample.

Figure 8:
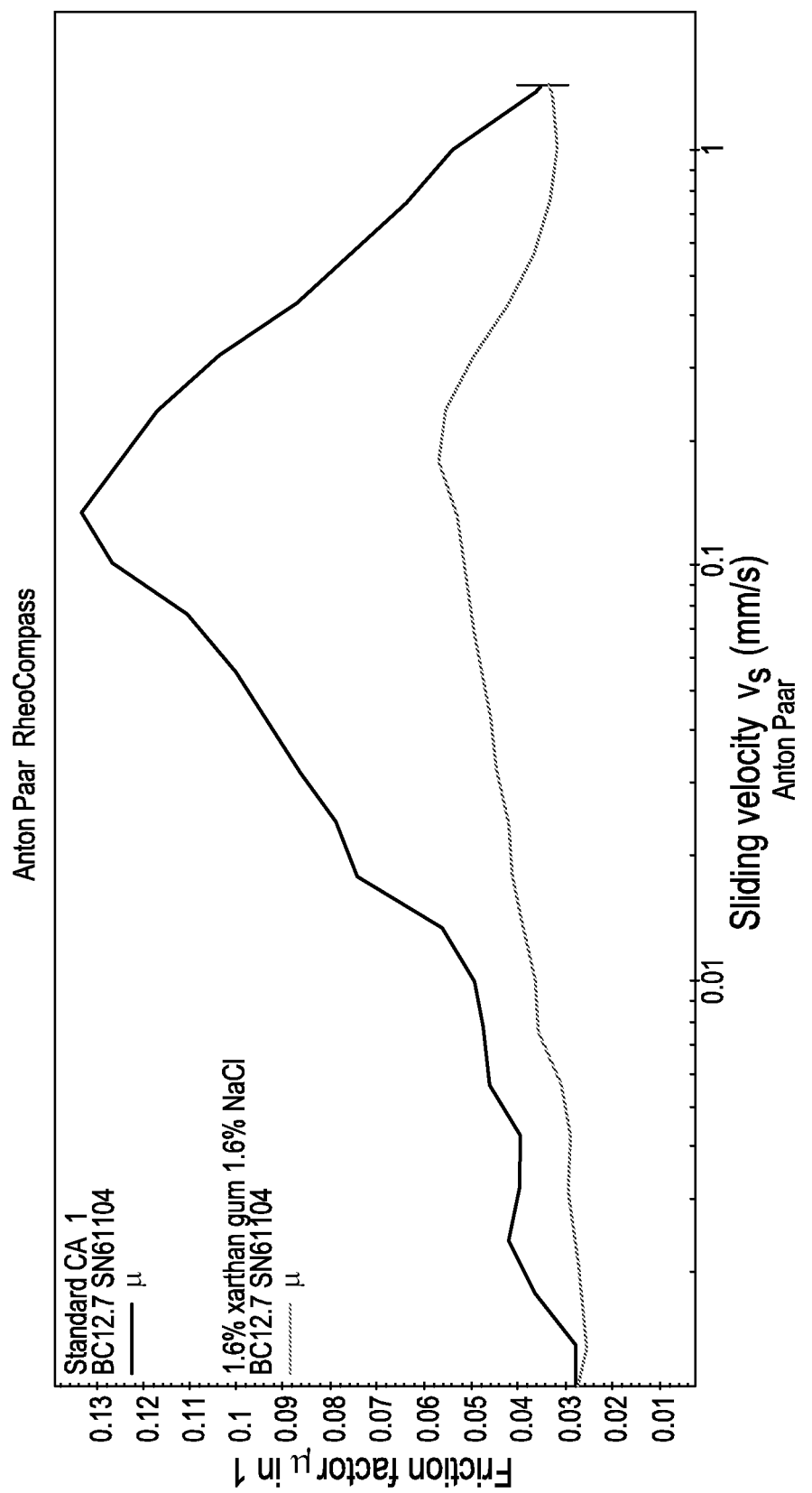
FIG. 8 shows the region of importance for determining the significance of tribological properties on cleaning ability for compositions of the present invention.

FIG. 8 shows a magnified portion of the elastohydrodynamic region of the Stribeck curve of an example of the present invention and a comparative example determined on an Anton Paar MCR 302 with MCR Tribology Cell T-PTD 200 at 21° C. Both of these samples had comparable rheology. The upper curve is Example 1 and the lower curve is comparative example 10. Although the samples had matching rheology, their tribology was significantly different. The sample which exhibited the higher coefficient of friction was an excellent cleaning agent, whereas the sample which had a lower coefficient of friction was not suitable as a cleaning agent.

Figure 9:
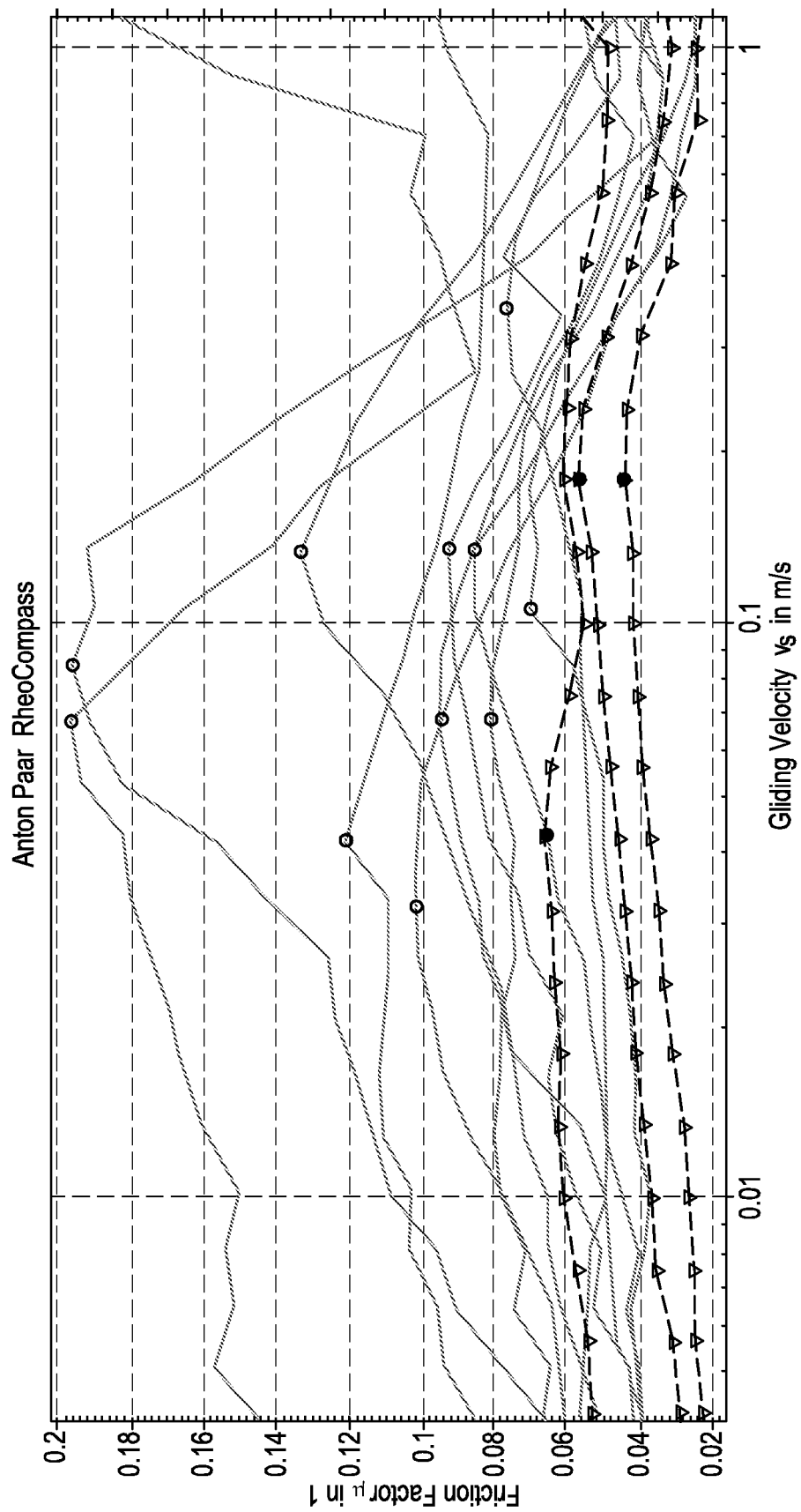
FIG. 9 shows an aggregate plot of all the tribiological curves of the embodiments of the present invention and comparative examples.

Those familiar with tribological measurements will appreciate that they can be sensitive to many factors such as the apparatus, temperature, and so on. The present experiments were conducted in every case keeping the conditions as similar as possible to ensure internal consistency of results. In any event, the examples given herein make it possible to normalize results obtained under differing conditions for direct comparison with the present invention FIG. 9 shows an aggregate plot of all the tribological curves of the embodiments of the present invention in the elastohydrodynamic region, which is typically from 0.004 m/s sliding velocity to 1 m/s sliding velocity. The maxima for the curves of formulations of the present invention, which all showed good cleaning properties, are shown as open circles, and the maxima for comparative examples, which possessed the same rheology but different tribology, are shown using closed circles. It can be seen that the compositions of the present invention all possessed an observable maximum in the elastohydrodynamic region. All of the samples of the present invention had a coefficient of friction $\eta$ (friction factor) maximum in the elastohydrodynamic region of 0.065 or above. The highest values for $\eta$ were about 0.195. No upper limit on $\eta$ is set but in practical terms, if the friction is too high the pumpability of the viscoelastic fluid becomes more difficult and other practical considerations may apply.

Test Soils, Soiling and Validation Process.

The removal of biocontaminant from endoscopes was modelled using test soils applied to the inner surfaces of Teflon tubing or metal surfaces of valve sockets, cylinders and connectors in order to mimic the inner structure of endoscopes. Procedures for soil preparation, as well as the fixed protein and biofilm contamination methods follows:

Protein Test Soil.

Standardised Edinburgh soil [Alfa M J, Olson N. Physical and composition characteristics of clinical secretions compared with test soils used for validation of flexible endoscope cleaning. The Journal of hospital infection. 2016; 93(1):83-8.] with modifications was used in experiments to evaluate the performance of the viscoelastic liquid.

Teflon Tubes

Teflon tubes (ID 3.7 mm and 10 cm long) were inoculated by pumping the protein soil into the tube with a syringe, holding the soil in position for 5 seconds and then pumping the soil back into the syringe. The inoculated tubes were fixed in place inside a small container. The container was then placed on top of a rotational mixing apparatus situated inside an incubator. The tubes were rotated at medium speed in the incubator for 30 minutes at 40° C. The tubes were then connected to a 4-port air pump machine (eight tubes at a time via four T-Pieces) within the 40° C. incubator. The tubes were held in the incubator for a further 15 minutes at low airflow. Any tubes that leaked during the airflow stage were discarded. The tubes were stored in a cool dry environment.

Extraction and testing of soil from Teflon tubes was done in the following manner:

Flexible tubing was placed on the tip of the lumens and a sample tube containing 3 mL of 0.1% SDS was placed in the other end of the lumen.

A sterile 10 mL syringe was used to flush 3 mL of 0.1% SDS (for 0.02 g) from a sample tube to the syringe (use 5 ml for 0.2 g). The SDS was flushed back and forth to remove soil (300 flushes) and dissolve in SDS. Flushing was performed until no visible soil was remaining after which additional flushes (50 times) were performed.

A further 3 mL of solvent was used if the previous quantity was insufficient to dissolve the soil The sample tube was removed and labelled accordingly and then tested for its protein content as per the Quantipro BCA assay method: https://www.sigmaaldrich.com/content/dam/sigma-aldrich/docs/Sigma/Bulletin/bca1bul.pdf Suction Valve Cylinders Before soiling, the suction valve cylinders were precleaned as follows:

Suction valve cylinders were connected together using flexible tubing and attached to a peristaltic pump A jar containing 200 mL of 4% enzyme (pre-heated to 45 C) was placed in a water bath regulated to 45° C.

The enzyme was recirculated through the suction valve cylinders for 2×20 minutes. The enzyme solution was replaced with a fresh batch after the first 20 minute cycle.

The daisy chain setup was then flushed with 5×60 mL DI water.

The connectors were filled with BCA (1.5 mL) and incubated for 30 minutes at 50° C. The resulting solution was analysed for remaining protein content as per the Quantipro BCA assay method: https://www.sigmaaldrich.com/content/dam/sigma aldrich/docs/Sigma/Bulletin/bca1bul.pdf Soiling and drying of the suction valve cylinders was done as follows:

The suction valve cylinder was weighed.

Protein soil was placed using a uL pipette tip in the internals of the suction valve cylinder (using an endoscope brush to spread the soil as uniformly as possible) until a weight difference of approximately 0.02 g/0.2 g is achieved After soiling, the cylinders were placed in a 40° C. oven for 30 minutes. The cylinders were then connected to pumps with low air flow (in the 40° C. oven) and allowed to stand for 15 minutes.

Figure 10:
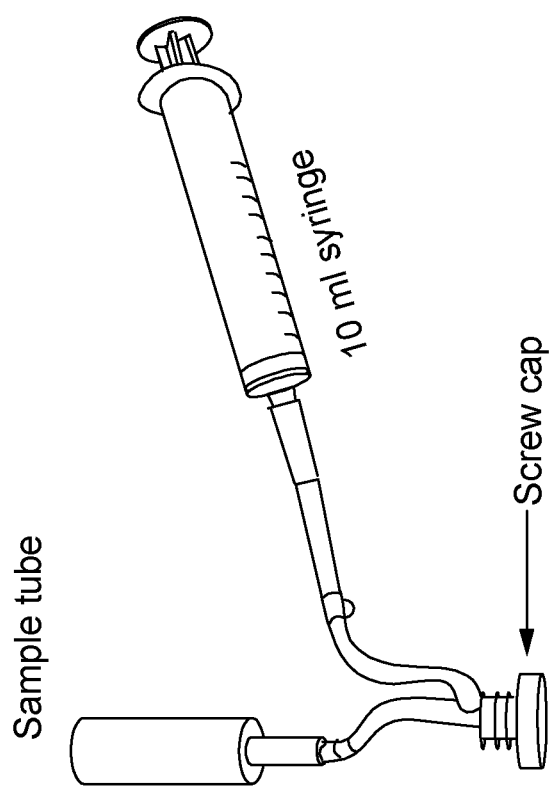
FIGS. 10 to 14 show test arrangements used in the present invention to measure the efficacy of endoscope cleaning.

Extraction and testing of soil from suction valve cylinders was done as follows:

Flexible tubing was placed on both sides of the suction valve cylinders and cap the bottom as shown in FIG. 10.

Using the sterile 10 mL syringe, 3 mL of 0.1% SDS solution (for 0.02 g) was transferred from a sample tube to the syringe (5 ml was used for 0.2 g). The SDS solution was flushed back and forth (300 flushes) to remove soil and dissolve it in the SDS. Flushing was performed until no visible soil remained after which additional flushes (50) were performed A further 3 mL of solvent could be used if the soil was not sufficiently dissolved.

Figure 11:
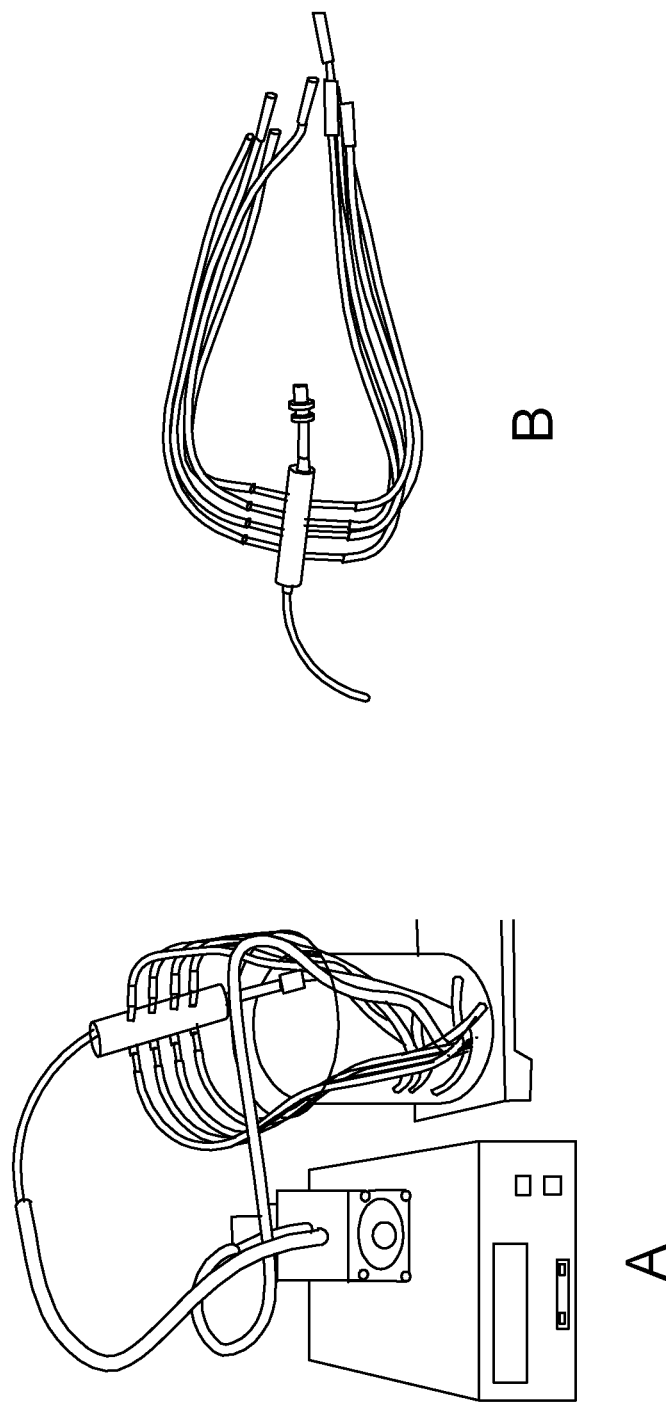

The sample tube was removed and labelled accordingly and tested for protein content as per the Quantipro BCA assay Method: https://www.sigmaaldrich.com/content/dam/sigma-aldrich/docs/Sigma/Bulletin/bca1bul.pdf Biopsy Ports Before soiling, the biopsy ports were pre-cleaned as follows:

The Biopsy ports were connected to 8 separate flexible tubes which were all connected together to one line leading to a peristaltic pump (see FIGS. 11a and 11b)

A 2 L beaker containing 600 mL of 2% enzyme (pre-heated to 45° C.) was placed in a water bath regulated to 45° C.

The flexible tubes connected to the cylinders were placed in the beaker.

The enzyme was recirculated through the biopsy port for 2×20 minutes. The enzyme solution was replaced with a fresh batch after the first 20 minute cycle;

The setup was then flushed with 1 L of water by replacing the beaker containing the enzyme with a beaker containing 1 L of water The cylinders were filled with BCA (2 mL) and incubated for 30 minutes at 50° C. The resulting solution was analysed for remaining protein content as per the Quantipro BCA assay method: https://www.sigmaaldrich.com/content/dam/sigma-aldrich/docs/Sigma/Bulletin/bca1bul.pdf.

Soiling and drying of biopsy ports was done as follows:

The biopsy port was weighed.

Figure 12:
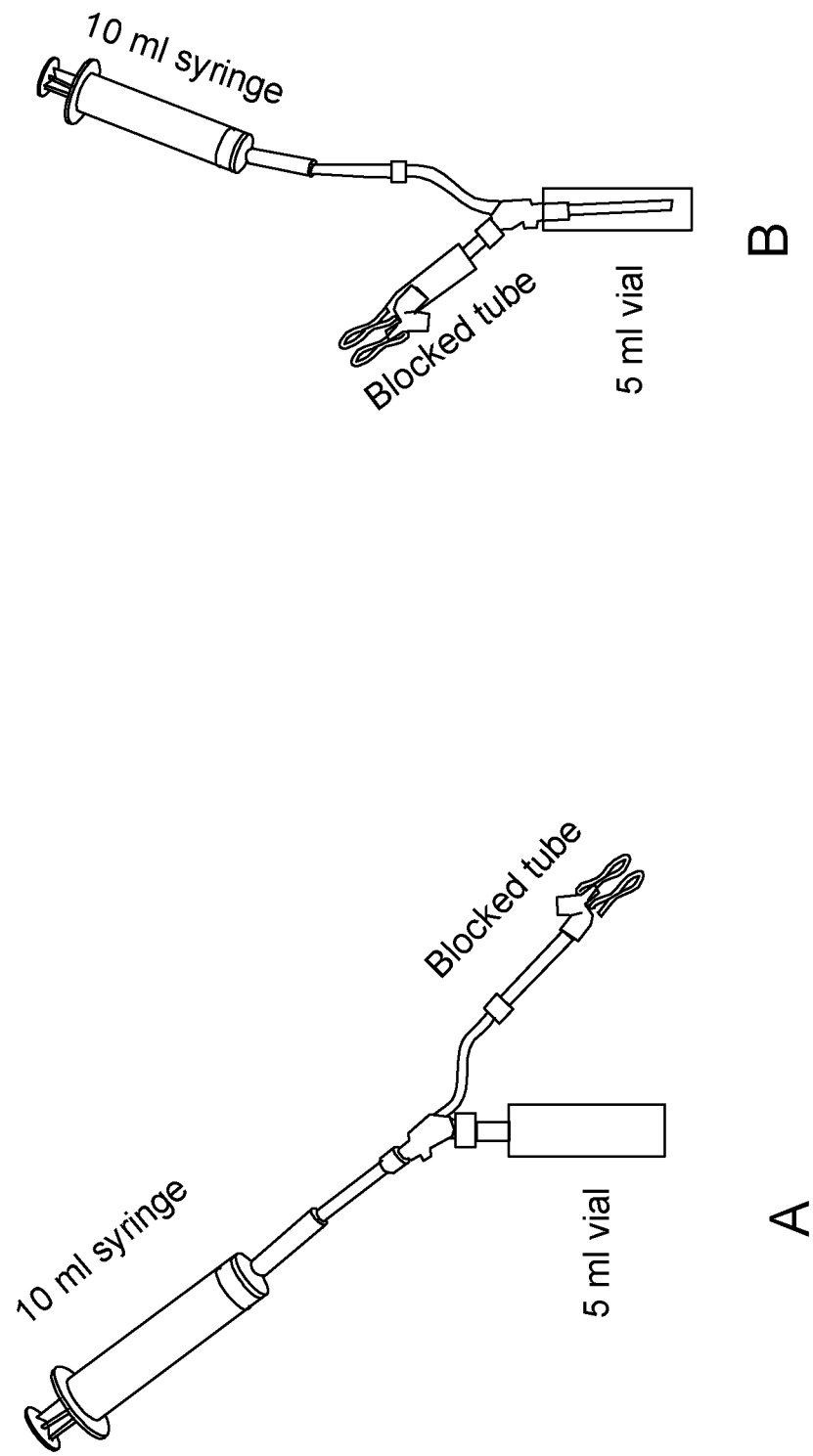

Protein soil was placed using a uL pipette tip in the internals of the biopsy port. An endoscope brush was used to spread soil as uniformly as possible) until a weight difference of approximately 0.02 g/0.2 g was achieved The above 2 steps were repeated for all biopsy ports (6-10).

the ports were placed in a 40° C. oven for 30 minutes and then connected to pumps with low air flow (in the 40° C. oven) and allowed to stand for 15 minutes Extraction and testing of protein soil from biopsy cylinders:

Flexible tubing was placed on the biopsy cylinders. One outlet of the biopsy cylinders was blocked and the remaining outlet was placed in a sample tube containing 3 mL of 0.1% SDS as shown in FIG. 12a.

A sterile 10 mL syringe was used to transfer 3 mL of 0.1% SDS (for 0.02 g) from the sample tube to the syringe (use 5 ml for 0.2 g). The SDS was flushed back and forth to remove soil (300 flushes) and dissolve in SDS. The blocked and unblocked outlets of the biopsy cylinders were reversed as per FIG. 12b and the SDS again flushed 300 times. Flushing was performed until no visible soil is remaining after which additional flushes (50 times) are performed. A further 3 mL of solvent could be use if required to dissolve the soil.

The sample tube was removed and labelled accordingly and tested for protein content as per the Quantipro BCA assay Method. https://www.sigmaaldrich.com/content/dam/sigma-aldrich/docs/Sigma/Bulletin/bca1bul.pdf Fixed Protein.

Tubes contaminated with fixed protein could be prepared as follows:

1% horse serum was pumped through a Teflon tube (ID 3.7 mm). The volume used was 2× tube volumes. After 20 minutes, 2× tube volumes of 1% glutaraldehyde were pumped through the tube. After 10 minutes, the process was repeated. Altogether, five cycles of horse serum followed by five cycles of glutaraldehyde were used. The tube was then washed with 10 tube volumes. The tube was cut into pieces of required length. These tubes were used for further Biofilm growing.

Biofilm.

Figure 13:
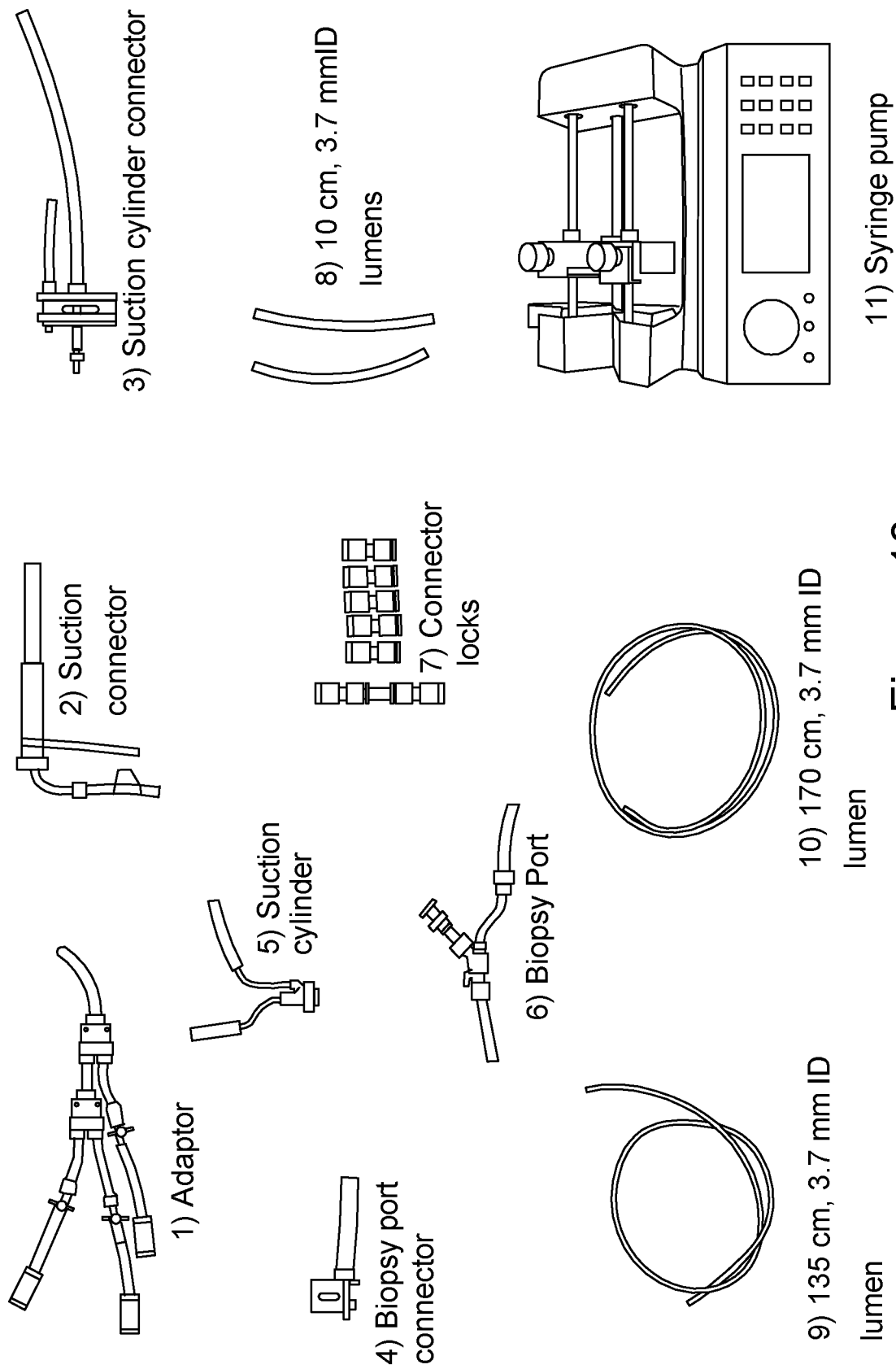
Figure 14:
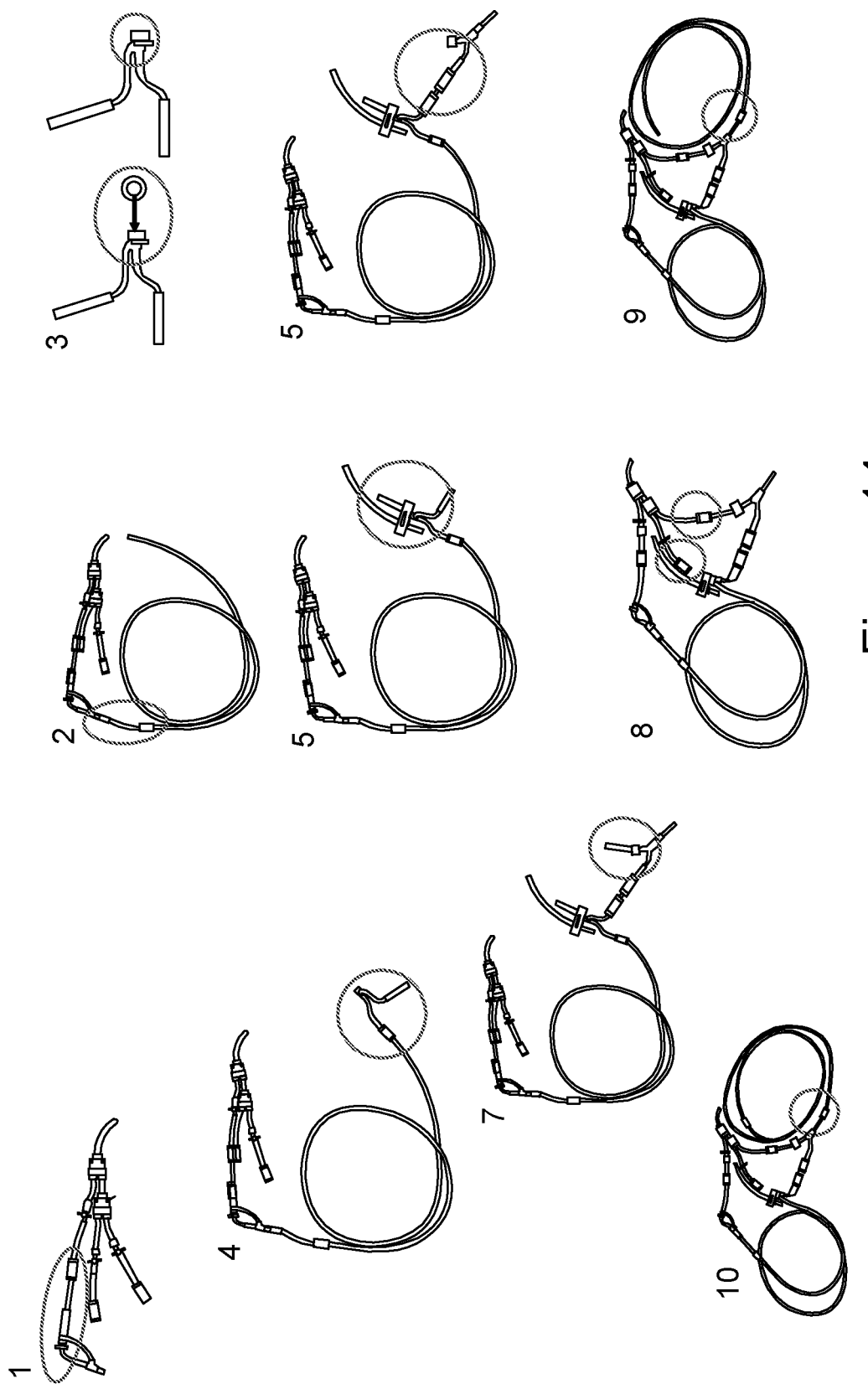

A *Pseudomonas aeruginosa* ATCC15442 biofilm was used in experiments to evaluate the cleaning efficacy of the viscoelastic liquid. A bench-top endoscope model was prepared having the following components, as illustrated in FIG. 13:

1) Adapter
2) Suction connector
3) suction cylinder connector
4) biopsy port connector
5) Suction cylinder
6) Biopsy port
7) Connector locks
8) 10 cm, 3.7 mm ID lumens
9) 135 cm 3.7 mm ID lumens
10) 170 cm 3.7 mm ID lumens
11) Syringe pump The 10 cm lumens, suction valve cylinders and the biopsy ports were soiled as described above. The test endoscope was then assembled as shown in FIG. 14 (the relevant portions in each figure have been circled):

1) The suction connector was connected to the adapter.
2) Using a connector lock, a soiled 10 cm lumen was connected using a connector lock to the suction connector and another connector lock was used to add the 135 cm lumen immediately after the soiled 10 cm lumen.
3) The suction valve cylinder nut was screwed to the suction valve cylinder.
4) The end of the 135 cm lumen was connected by a connector lock the suction valve cylinder.
5) The suction valve cylinder was attached to the suction valve cylinder connector.
6) The double sided connector lock was used to connect the biopsy port to the suction valve cylinder.
7) The Biopsy port end of the biopsy port was attached to the biopsy port connector.
8) The suction valve cylinder connector and biopsy port connector were attached to the adapter.
9) Using another connector lock, the biopsy port was connected to the 170 cm lumen.
10) The second soiled 10 cm lumen was attached to the 170 cm lumen using another connector lock.

Cleaning of the Endoscope Model with the Viscoelastic Liquid.

The main end of the adapter was connected to a 60 mL syringe that was been pre-loaded with the viscoelastic liquid. As shown in the figure above, the directions of viscoelastic liquid flow were controlled using three valves (three connector ports, 1=position 1 or suction connector end, 2=position 2 or suction valve cylinder connector, 3=position 3 or biopsy port connector). A contaminated waste container should be placed at the distal tip end of the endoscope model to hold residual viscoelastic liquid/soil which exits through the scope.

The sequence of viscoelastic liquid pumping was as follows (flow rate—3 mL/min):

a) Open valve 1 while having valves 2 and 3 closed then prime position 1 by pumping 4.5 mL of the viscoelastic liquid from the beginning of the adapter.
b) Close valve 1 and open valve 2 to prime position 2 by pumping 5.5 mL of the viscoelastic liquid.
c) Close valve 2 and open valve 3 to prime position 3 by pumping 2.9 mL of the viscoelastic liquid.
d) After priming, close valves 2 and 3 while having valve 1 open. Pump 19.5 mL of the viscoelastic liquid through position 1.
e) Close valve 1 and open valve 2. Pump 5 mL of the viscoelastic liquid through position 2.
f) Close valve 2 and open valve 3. Pump 19.5 mL of the viscoelastic liquid through position 3.
g) Close valve 3 and open valve 1 again. Pump 4 mL of the viscoelastic liquid through position 1.
h) Remove the syringe with the viscoelastic liquid from the syringe pump and replace with a syringe containing water.
i) Pump 20 mL of water (3 mL/min) through position 1.
j) Pump 10 mL of water through position 2.
k) Pump 10 mL of water through position 3.
l) The endoscope model was disconnected from the syringe pump and connected to a tap water line and 690 mL of water is used to flush each position (1, 2 and 3).

Extraction of Remaining Protein Soil from the Endoscope Model.

Any remaining residue is extracted from the different connectors and lumens and analysed for protein content as per the protocol stated above.

Results for Remaining Protein and Microbiological Load After the Bench-Top Cleaning of the Endoscope Model with the Viscoelastic Liquid

| Endoscope Piece | Visual cleaning | Protein remaining | Residual paste |
|---|---|---|---|
| Biopsy port | Yes | 2.29 µg/cm$^2$ (2.05, 2.39, 2.72, 2.02) | No |
| 10 cm lumen (proximal end) | Yes | 2.79 µg/cm$^2$ (3.30, 2.63, 2.56, 2.66) | No |
| 10 cm lumen (distal end) | Yes | 2.86 µg/cm$^2$ (3.25, 2.79, 2.69, 2.71) | No |
| Suction valve cylinder | Yes | 1.96 µg/cm$^2$ (1.66, 1.86. 1.97. 2.35) | No |

The reduction in the 3.7 mm lumens for biofilm (*P. aeruginosa* ATCC 15442, start count 8.19 log$_{10}$ cfu/ml) was as follows:

| Application | Log reduction | Average |
|---|---|---|
| Tap Water | 1.49 | 1.16 |
| | 1.09 | |
| | 0.88 | |
| Example 2 | 7.19 | 7.86 |
| | 8.19 | |
| | 7.19 | |
| | 7.19 | |
| | 8.19 | |
| Example 1 | 7.19 | 7.09 |
| | 7.19 | |
| | 6.89 | |
| | 7.19 | |
| | 7.19 | |

The claims of the invention are as follows:

1. A method of reducing a biocontaminant on a surface contaminated therewith comprising contacting the surface with a viscoelastic liquid and flowing said viscoelastic liquid along said surface thereby to remove said biocontaminant from the surface, wherein the viscoelastic liquid has the following properties at 21° C.:
    a rotational yield point between 140% strain and 300% strain;
    a peak viscosity between 550 Pa·s and 2000 Pa·s;
    an oscillatory flow point between 250 and 700% strain; and
    a coefficient of friction µ which has a maximum value in the viscoelastic liquid's elastohydrodynamic region.

2. A method according to claim 1 wherein the viscoelastic liquid has a coefficient of friction µ, of 0.06 or greater in its elastohydrodynamic region.

3. A method according to claim 1 wherein the viscoelastic liquid is flowed under conditions of controlled shear rate and/or strain.

4. A method according to claim 1 wherein the surface comprises an interior surface of a medical instrument.

5. A method according to claim 1 wherein the viscoelastic liquid is flowed continuously in a single direction.

6. A method according to claim 1 wherein the flow of the viscoelastic liquid is pulsed.

7. A method according to claim 1 wherein the viscoelastic liquid has a flow rate such that an elastic modulus G' of the viscoelastic liquid exceeds a viscous modulus G" of the viscoelastic liquid.

8. A method according to claim 1 wherein the viscoelastic liquid has a flow rate such that a shear rate of the viscoelastic liquid is below a flow point of the viscoelastic liquid.

9. A method according to claim 1 further including one or more pre-rinsing steps with water and/or enzymatic detergent.

10. A method according to claim 1 further including one or more post-rinsing steps with water and/or enzymatic detergent.

11. A method according to claim 1 wherein the viscoelastic liquid comprises one or more polymers that are cationic, amphoteric, anionic or non-ionic, and wherein the one or more polymers are dispersed in a solvent.

12. A method according to claim 1 wherein the viscoelastic liquid contains a dispersed high-surface area material that is inorganic or organic.

13. A method according to claim 1 wherein the viscoelastic liquid contains dispersed abrasive particles of inorganic and/or organic materials.

14. A method according to claim 11 wherein the one or more polymers comprise is carbomer, crosspolymer, acrylic polymer, Guar Gum, or their mixture.

15. A method according to claim 11 wherein the viscoelastic liquid has a solid content between 0.1 and 40%.

16. A method according to claim 11 wherein the one or more polymers are synthetic or natural.

17. A method according to claim 16 wherein the one or more polymers are Polyacrylate crosspolymer-6, carbomer, or mix of both.

18. A method according to claim 11 wherein a concentration of the one or more polymers is in the range of 0.1 to 20% by weight.

19. The method of claim 4 wherein the medical instrument comprises a lumen, and wherein the method further comprises directing the viscoelastic liquid along the interior surface of the lumen at a selected rate.

\* \* \* \* \*